United States Patent
Gibby et al.

(10) Patent No.: US 12,016,633 B2
(45) Date of Patent: Jun. 25, 2024

(54) ALIGNMENT OF MEDICAL IMAGES IN AUGMENTED REALITY DISPLAYS

(71) Applicant: Novarad Corporation, American Fork, UT (US)

(72) Inventors: Wendell Arlen Gibby, Mapleton, UT (US); Steven Todd Cvetko, Draper, UT (US)

(73) Assignee: Novarad Corporation, Provo, UT (US)

( * ) Notice: Subject to any disclaimer, the term of this patent is extended or adjusted under 35 U.S.C. 154(b) by 354 days.

(21) Appl. No.: 17/138,558

(22) Filed: Dec. 30, 2020

(65) Prior Publication Data
US 2022/0202493 A1    Jun. 30, 2022

(51) Int. Cl.
*A61B 34/10* (2016.01)
*G06F 3/01* (2006.01)
(Continued)

(52) U.S. Cl.
CPC .............. *A61B 34/10* (2016.02); *G06F 3/017* (2013.01); *G06F 3/0304* (2013.01);
(Continued)

(58) Field of Classification Search
CPC ....... A61B 34/10; G06F 3/017; G06F 3/0304; G06T 7/0012; G06T 7/006
(Continued)

(56) References Cited

U.S. PATENT DOCUMENTS

| 6,147,678 A | 11/2000 | Kumar et al. |
| 6,919,867 B2 | 7/2005 | Sauer |

(Continued)

FOREIGN PATENT DOCUMENTS

| EP | 3470006 | 4/2019 |
| JP | 2014-131552 | 7/2014 |

(Continued)

OTHER PUBLICATIONS

Blackwell et al.; "An Image Overlay System for Medical Data Visualization;" Medical Image Computing and Computer-Assisted Intervention; (MICCAI 1998); First International Conference; (Oct. 1998); pp. 232-240; Cambridge, MA; <doi: 10.1007/BFb0056206 >.

(Continued)

*Primary Examiner* — Gabriel I Garcia
(74) *Attorney, Agent, or Firm* — Thorpe North & Western, LLP.

(57) ABSTRACT

An AR headset is described to co-localize an image data set with a body of a person. The image data set of a portion of the body may be identified. The image data set can include a virtual anatomical marker to identify an anatomical location. A spatial location may be identified using a physical pointer object in a field of view of the AR headset. A spatial location of a visible anatomical feature as identified using the physical pointer object may be recorded. The registration may be triggered based on an input that the physical pointer object is located at a visible anatomical feature of the body of the person. Further, the image data set may be aligned with the body of the person using the spatial location recorded for the visible anatomical feature as referenced to the virtual anatomical marker in the image data set.

34 Claims, 18 Drawing Sheets

(51) Int. Cl.
  *G06F 3/03*   (2006.01)
  *G06T 7/00*   (2017.01)
  *G06T 19/00*  (2011.01)

(52) U.S. Cl.
  CPC .......... *G06T 7/0012* (2013.01); *G06T 19/006* (2013.01); *A61B 2034/102* (2016.02); *A61B 2034/105* (2016.02); *A61B 2034/107* (2016.02)

(58) Field of Classification Search
  USPC ........................................................ 382/128
  See application file for complete search history.

(56) References Cited

U.S. PATENT DOCUMENTS

| | | |
|---|---|---|
| 8,657,809 B2 | 2/2014 | Schoepp |
| 9,119,655 B2 | 9/2015 | Bowling et al. |
| 9,123,155 B2 | 9/2015 | Cunningham et al. |
| 9,128,909 B2 | 9/2015 | Brindley |
| 9,161,824 B2 | 10/2015 | Chishti et al. |
| 9,367,963 B2 | 6/2016 | Finn et al. |
| 9,572,516 B1 * | 2/2017 | Sheikh .................. A61B 5/055 |
| 9,589,348 B1 | 3/2017 | Linde |
| 9,861,446 B2 | 1/2018 | Lang |
| 9,980,780 B2 | 5/2018 | Lang |
| 10,010,379 B1 | 7/2018 | Gibby et al. |
| 10,154,239 B2 | 12/2018 | Casas |
| 10,159,530 B2 | 12/2018 | Lang |
| 10,194,131 B2 | 1/2019 | Casas |
| 10,278,777 B1 | 5/2019 | Lang |
| 10,292,768 B2 | 5/2019 | Lang |
| 10,326,975 B2 | 6/2019 | Casas |
| 10,368,947 B2 | 8/2019 | Lang |
| 10,405,927 B1 | 9/2019 | Lang |
| 10,478,149 B2 | 11/2019 | Tamersoy |
| 10,511,822 B2 | 12/2019 | Lang |
| 10,594,998 B1 | 3/2020 | Casas |
| 10,602,114 B2 | 3/2020 | Casas |
| 10,603,113 B2 | 3/2020 | Lang |
| 10,646,285 B2 | 5/2020 | Siemionow et al. |
| 10,742,949 B2 | 8/2020 | Casas |
| 10,743,939 B1 | 8/2020 | Lang |
| 10,799,296 B2 | 10/2020 | Lang |
| 10,841,556 B2 | 11/2020 | Casas |
| 10,929,670 B1 | 2/2021 | Troy et al. |
| 11,145,123 B1 | 10/2021 | Chor |
| 11,172,996 B1 | 11/2021 | Qian et al. |
| 11,266,480 B2 | 3/2022 | Gibby et al. |
| 11,287,874 B2 | 3/2022 | Gibby et al. |
| 11,432,879 B2 | 9/2022 | Kapoor |
| 2005/0215879 A1 | 9/2005 | Chuanggui |
| 2005/0251030 A1 | 11/2005 | Azar et al. |
| 2005/0259882 A1 | 11/2005 | Dewaele |
| 2005/0262031 A1 | 11/2005 | Saidi et al. |
| 2006/0152434 A1 | 7/2006 | Sauer et al. |
| 2007/0060799 A1 | 3/2007 | Lyon |
| 2007/0066881 A1 | 3/2007 | Edwards |
| 2007/0090197 A1 | 4/2007 | Senda |
| 2007/0167735 A1 | 7/2007 | Zhong et al. |
| 2007/0228171 A1 | 10/2007 | Thiyagarajah |
| 2008/0208041 A1 | 8/2008 | Gilboa |
| 2008/0269664 A1 | 10/2008 | Trovato et al. |
| 2009/0078772 A1 | 3/2009 | Ofek et al. |
| 2009/0278915 A1 | 11/2009 | Kramer et al. |
| 2010/0049548 A1 | 2/2010 | Kuboto |
| 2010/0099980 A1 | 4/2010 | Godara et al. |
| 2010/0215213 A1 | 8/2010 | Mielekamp et al. |
| 2011/0105895 A1 | 5/2011 | Kornblau et al. |
| 2011/0268248 A1 | 11/2011 | Simon et al. |
| 2011/0306986 A1 | 12/2011 | Lee et al. |
| 2012/0078236 A1 | 3/2012 | Schoepp |
| 2012/0244939 A1 | 9/2012 | Braun |
| 2013/0197354 A1 | 8/2013 | Maschke et al. |
| 2013/0345718 A1 | 12/2013 | Crawford et al. |
| 2014/0062900 A1 | 3/2014 | Kaula et al. |
| 2014/0148818 A1 | 5/2014 | Komuro et al. |
| 2014/0160002 A1 | 6/2014 | Dent |
| 2014/0210856 A1 | 7/2014 | Finn et al. |
| 2014/0275760 A1 | 9/2014 | Lee et al. |
| 2014/0318699 A1 | 10/2014 | Longinotti-Buitoni |
| 2014/0355840 A1 | 12/2014 | Pearson Peyton |
| 2015/0161802 A1 | 6/2015 | Christiansen |
| 2015/0168729 A1 | 6/2015 | Kobayashi |
| 2015/0173715 A1 | 6/2015 | Raghavan et al. |
| 2016/0035139 A1 | 2/2016 | Fuchs et al. |
| 2016/0143699 A1 | 5/2016 | Tanji |
| 2016/0166333 A1 | 6/2016 | Wang et al. |
| 2016/0180441 A1 | 6/2016 | Hasan et al. |
| 2016/0188941 A1 | 6/2016 | Todeschini |
| 2016/0220393 A1 | 8/2016 | Slivka et al. |
| 2016/0249989 A1 | 9/2016 | Devam et al. |
| 2016/0259428 A1 | 9/2016 | Hou et al. |
| 2016/0270853 A1 | 9/2016 | Lavalee et al. |
| 2017/0045938 A1 | 2/2017 | Aoyama et al. |
| 2017/0065832 A1 | 3/2017 | Berlinger |
| 2017/0071686 A1 | 3/2017 | Birkenbach et al. |
| 2017/0116729 A1 | 4/2017 | Stolka et al. |
| 2017/0166729 A1 | 4/2017 | Stolka et al. |
| 2017/0165008 A1 | 6/2017 | Finley |
| 2017/0178540 A1 | 6/2017 | Rios et al. |
| 2017/0196513 A1 | 7/2017 | Longinotti-Buitoni |
| 2017/0249745 A1 | 8/2017 | Fiala |
| 2017/0258526 A1 | 9/2017 | Lang |
| 2017/0273654 A1 | 9/2017 | Taguchi et al. |
| 2017/0296292 A1 | 10/2017 | Mahmood et al. |
| 2017/0368369 A1 | 12/2017 | Heinrich |
| 2018/0064385 A1 | 3/2018 | Schwartz |
| 2018/0064410 A1 | 3/2018 | Li et al. |
| 2018/0092698 A1 | 4/2018 | Chopra et al. |
| 2018/0177403 A1 | 6/2018 | Kim-Whitty |
| 2018/0247128 A1 | 8/2018 | Alvi et al. |
| 2018/0303558 A1 | 10/2018 | Thomas |
| 2018/0321894 A1 | 11/2018 | Paulovich |
| 2018/0322702 A1 | 11/2018 | Djajadiningrat |
| 2018/0373327 A1 | 12/2018 | Todeschini |
| 2019/0015009 A1 | 1/2019 | Dyer et al. |
| 2019/0053851 A1 | 2/2019 | Siemionow et al. |
| 2019/0075456 A1 | 3/2019 | Evans |
| 2019/0108645 A1 | 4/2019 | Ben-Yishai |
| 2019/0142519 A1 | 5/2019 | Siemionow et al. |
| 2019/0175285 A1 | 6/2019 | Siemionow et al. |
| 2019/0192230 A1 | 6/2019 | Siemionow et al. |
| 2019/0201106 A1 | 6/2019 | Siemionow et al. |
| 2019/0209080 A1 | 7/2019 | Gullotti et al. |
| 2019/0236816 A1 | 8/2019 | Wang |
| 2019/0287306 A1 | 9/2019 | Wieser |
| 2019/0310819 A1 | 10/2019 | Xu et al. |
| 2019/0317719 A1 | 10/2019 | Baer |
| 2019/0328462 A1 * | 10/2019 | Liu .................. G16H 40/63 |
| 2019/0348169 A1 | 11/2019 | Gibby et al. |
| 2019/0380792 A1 | 12/2019 | Poltaretskyi et al. |
| 2020/0051274 A1 | 2/2020 | Siemionow et al. |
| 2020/0058169 A1 | 2/2020 | Friesenhahn |
| 2020/0138518 A1 | 5/2020 | Lang |
| 2020/0145495 A1 | 5/2020 | Coffey |
| 2020/0151507 A1 | 5/2020 | Siemionow et al. |
| 2020/0159313 A1 | 5/2020 | Gibby et al. |
| 2020/0186786 A1 * | 6/2020 | Gibby .................. H04N 13/167 |
| 2020/0188030 A1 | 6/2020 | Kopper |
| 2020/0197107 A1 | 6/2020 | Ryan et al. |
| 2020/0225814 A1 | 7/2020 | Norieda |
| 2020/0242755 A1 | 7/2020 | Schneider |
| 2020/0275988 A1 | 9/2020 | Johnson et al. |
| 2020/0286222 A1 | 9/2020 | Essen |
| 2020/0375666 A1 | 12/2020 | Murphy |
| 2020/0405395 A1 | 12/2020 | Gullotti et al. |
| 2021/0045838 A1 | 2/2021 | Bradbury et al. |
| 2021/0049921 A1 * | 2/2021 | Welch .................. G06F 3/016 |
| 2021/0137634 A1 | 5/2021 | Lang |
| 2021/0186355 A1 | 6/2021 | Ben-Yishai et al. |
| 2022/0130116 A1 | 4/2022 | McCall |
| 2022/0151705 A1 | 5/2022 | Nikou et al. |
| 2022/0202493 A1 | 6/2022 | Gibby et al. |
| 2022/0287676 A1 | 9/2022 | Steines et al. |

(56) References Cited

U.S. PATENT DOCUMENTS

| | | |
|---|---|---|
| 2022/0291741 A1 | 9/2022 | Gibby et al. |
| 2023/0072188 A1 | 3/2023 | Gibby et al. |
| 2023/0169740 A1 | 6/2023 | Gibby et al. |

FOREIGN PATENT DOCUMENTS

| | | |
|---|---|---|
| JP | 2017-146758 | 8/2017 |
| WO | WO 2008/076079 | 6/2008 |
| WO | WO 2014/200016 | 12/2014 |
| WO | WO 2014200016 | 12/2014 |
| WO | WO 2016/162789 | 10/2016 |
| WO | WO 2018-063528 | 4/2018 |
| WO | WO 2018/132804 | 7/2018 |
| WO | WO 2018/134140 | 7/2018 |
| WO | WO 2019/051464 | 3/2019 |
| WO | WO 2019/238209 | 12/2019 |
| WO | WO 2020123702 | 6/2020 |

OTHER PUBLICATIONS

"QR code tracking," Microsoft Hololens Documentation, obtained at https://docs.microsoft.com/en-us/windows/mixed-reality/qr-code-tracking, Oct. 18, 2021.

Microsoft Hololens for Developers, Full Document, Microsoft Hololens Documentation, obtained at https://docs.microsoft.com/en-us/windows/mixed-reality/qr-code-tracking, Oct. 18, 2021.

Peters, T.M.: Image-guidance for surgical procedures. Phys. Med. Biol. 51 (14), R505-R540 (2006), 37 pages.

Fabrizio Cutolo, Augmented Reality in Image-Guided Surgery, Nov. 2017, 12 pages.

Sutherland et al. "Applying Modern Virtual and Augmented Reality Technologies to Medical Images and Models", Journal of Digital Imaging, Feb. 15, 2019, pp. 38-53. Retrieved on Jun. 17, 2021. Retrieved from URL: https://pubmed.ncbi.nlm.nih.gov/30215180/.

* cited by examiner

US 12,016,633 B2

ALIGNMENT OF MEDICAL IMAGES IN AUGMENTED REALITY DISPLAYS

BACKGROUND

Mixed or augmented reality is an area of computing technology where images or views of the physical world and virtual computing worlds may be combined into a mixed reality world. In mixed reality, people, places, and objects from the physical world and virtual worlds become a blended environment. A mixed reality experience may be provided through existing commercial or custom software along with the use of VR (virtual reality) or AR (augmented reality) headsets.

Augmented reality (AR) is an example of mixed reality where a live direct view or an indirect view of a physical, real-world environment is augmented or supplemented by computer-generated sensory input such as images, sound, video, graphics or other data. Such augmentation may be performed as a real-world location is viewed and augmented graphics may be provided in context with visible environmental elements. With the help of advanced AR technology (e.g. adding computer vision and object recognition) the information about the surrounding real world of the user becomes interactive and/or may be digitally modified (e.g. via computer graphic overlays).

An issue faced in using AR systems or AR headsets is identifying a position and orientation of a physical object with a high degree of precision. Similarly, aligning the position of a virtual element with a physical object in a live view of a real-world environment may be challenging. For example, aligning a virtual object with a physical object as viewed through an AR headset may be difficult because the luminescence or light of the virtual object tends to obscure the underlying physical object with which the virtual object is to be aligned. Providing an approximate alignment of a virtual object with a physical object to within a few centimeters may be useful for entertainment and less demanding applications but greater positioning and alignment resolution for AR systems may be desired in the scientific, engineering and medical disciplines. As a result, positioning and alignment processes for AR used in the scientific, engineering and medical disciplines may be done manually which can be time consuming, cumbersome, and inaccurate.

DETAILED DESCRIPTION

A technology is provided for using an augmented reality (AR) headset to co-localize an image data set with a body of a person. The technology may use a physical pointer object to identify a spatial location to align with a virtual anatomical marker in the image data set. The virtual anatomical marker may be created or marked in the image data set by a medical professional. The physical pointer object may have an optical code on the physical pointer object, and the optical code may be used to determine a location of the physical pointer object and in turn a location of a pointer or point (e.g., a tip) of the physical pointer object in the three-dimensional (3D) space being viewed by the AR headset. The AR headset may identify one or more optical codes (e.g., an AprilTag, QR code, or 2D optical bar code) that are in view of a camera of the AR headset during a medical procedure. The physical pointer object may be an object, such as a wand, a trochar, a needle or a finger of a medical professional or user.

The image data set may be aligned with a body of a person by aligning a virtual anatomical marker and a spatial location identified using the physical pointer object, as touched or marked by a tip or a point on the physical pointer object during a medical procedure. The image data set may be a previously acquired image of a portion of body of a person using a non-optical imaging modality. Examples of the non-optical imaging modalities may be an MRI (magnetic resonance imaging) modality, CT (computed tomography) scanning modality, X-ray modality, Positron Emission Tomography (PET) modality, an ultrasound modality, a fluorescence modality, an Infrared Thermography (IRT) modality, 3D Mammography, or a Single-Photon Emission Computed Tomography (SPECT) scan modality, etc. The image data set can be aligned to the body of the person using the virtual anatomical marker (e.g., an image visible marker) that is aligned with a spatial location defined by a tip of the physical pointer object or a spatial location defined at known distance from the tip of the physical pointer object.

The term alignment may mean that the virtual anatomical marker and the spatial point are aligned to within a few millimeters or the alignment of the virtual anatomical marker may be within a set distance from the spatial point (e.g., 1 cm below the surface). For example, the virtual anatomical marker may be aligned with the tip of physical pointer object but virtual anatomical marker may be aligned to be a few more millimeters under the skin or bone, etc. A virtual anatomical marker is a marker, tag or notation that is added to and viewed in a data set captured using a non-visible imaging modality, such as a captured radiology image or an image data set, which may not be visually visible to the AR headset.

Figure 1:
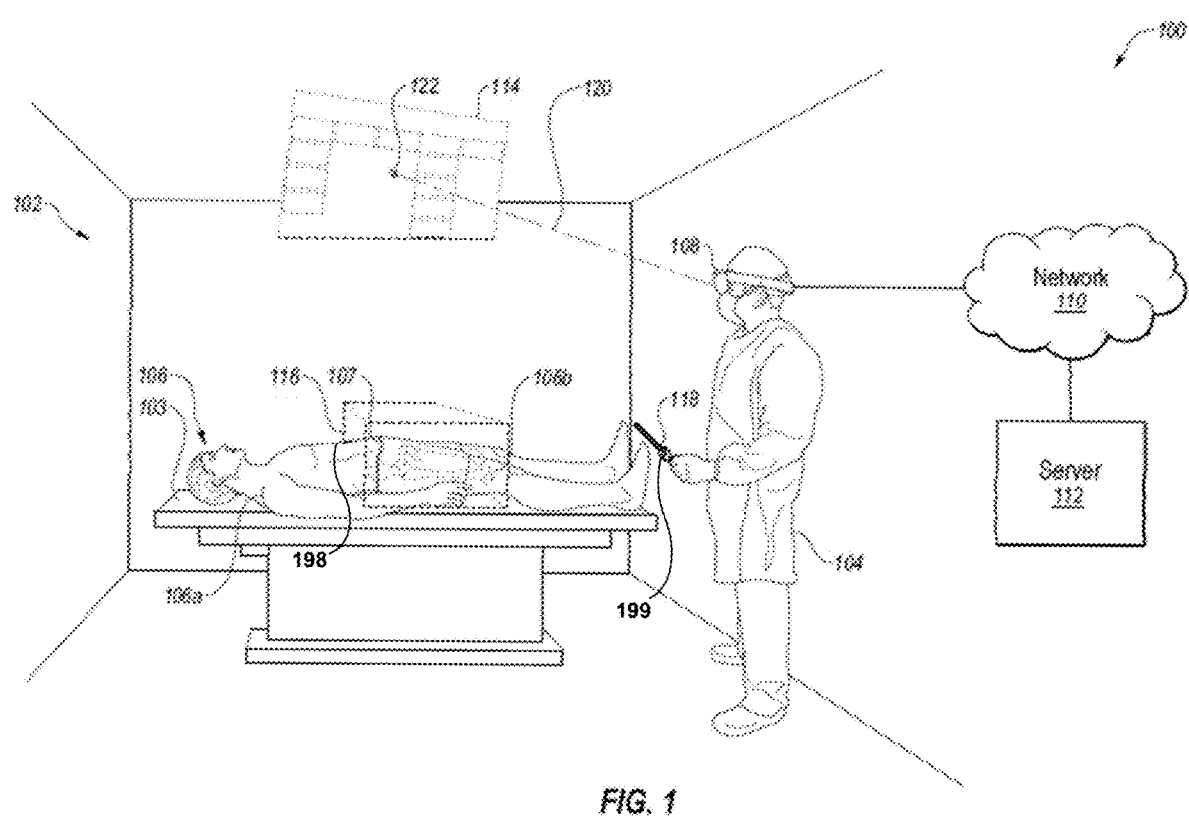
FIG. 1 illustrates an example augmented reality (AR) environment in which an image data set of a patient may be aligned to actual views of the patient using a physical pointer object which identifies a spatial location to align with a virtual anatomical marker in an image data set.

FIG. 1 illustrates an example of an augmented reality (AR) environment 100 in which an image data set 116 of a patient or a person 106 may be aligned with actual views of the patient 106 using a spatial location identified using a physical pointer object 118 in a field of view of an optical sensor of the AR headset. For example, the spatial location may be a spot, area or geometry in space that is identified using the physical pointer object. In another example, a target location or target area may be considered a spatial location.

The image data set of a portion of the body of the person may be obtained using a medical imaging device, and the image data set may have a virtual anatomical marker to identify an anatomical feature. In one example, the image visible marker may be created or placed by a medical professional who marks the image with virtual marking tools and virtual graphics to create a virtual anatomical marker with computer graphics. For example, a location for the virtual anatomical marker in the image data set may be defined prior to a medical procedure using a computing device or workstation controlled by a medical professional. The virtual anatomical marker in the image data set may be a virtual graphical mark that is a dot, a circle, a line, a curve, a spline, crosshairs, a point, a plane, a call-out, a two-dimensional (2D) graphic object or a three-dimensional (3D) graphic object. A medical professional or other individual may trace a curve or shape that is to be used for alignment such as shape of an anatomical feature of a patient. The term anatomical feature as used herein may refer to any anatomical aspect of a person or patient and not necessarily to unique anatomical features.

Alternatively, the image data set may be captured with a representation of the virtual anatomical marker in machine captured images that capture structures of the human body with a non-optical imaging modality. For example, an image visible marker, such as an image visible code, image visible fluid-filled structure, image visible fluid in a container or capsule (e.g., an MRI bead or sphere), a radio dense marker (e.g., a radiopaque marker for CT), a radio isotope, or an image visible object (e.g., image visible material), may be used to create the virtual anatomical marker in an image data set. In other imaging modalities as mentioned above, an appropriate contrast medium can be provided in a container that is visible in an image captured in the respective modality (MRI, CT, nuclear based image acquisition, etc.) to create a virtual anatomical marker.

The physical pointer object 118 may be a metal wand, a plastic wand, a trocar, a needle, a physical object with a pointing tip or another medical pointer which has a detectable pointer location in three-dimensional (3D) space. The physical pointer object 118 may have an optical code 199 affixed to the physical pointer (e.g., a wand or finger) to identify the spatial location of the physical pointer object 118.

Alternatively, the optical code 199 may be permanently printed onto or formed into a handle or other portion of the physical pointer object. For example, the optical code may be formed into the handle of the physical pointer object during injection molding or a 3D printing process to form recessed portions of the optical code that represent light portions of the optical code and un-recessed parts of the optical code that represent dark parts of the optical code (or vice versa). Further, the optical code may be embossed onto the handle of the physical pointer object using colored plastic, paint or similar material. The optical code 199 on the physical pointer object may also be identified in camera images captured by the AR headset 108 using a visible AprilTag or 2D barcode as the optical code. The spatial location of a physical wand can be recognized by the AR headset using the optical code. In an alternative configuration, a spatial location of a tip of the physical pointer object can be recognized by first detecting the edges of the physical pointer object. Once the edges of the physical pointer object are known then a tip or pointer of the physical pointer object may be identified.

The optical codes may also include data and/or values embedded into the optical codes. In one example, the embedded data may be values defining a medical instrument type, medical instrument model, medical instrument version, or medical instrument manufacturer. In addition, each physical pointer object may have a unique code for the device. When a unique code is recognized for the physical pointer object, the AR headset may unlock ability to use the physical pointer object or may unlock the pre-recorded navigation software or guidance software for that physical pointer object. The data in the optical code may also be used to check that the right medical instrument, right image data set file, and the right shape of medical instrument are being used for a medical procedure. The value(s) in the optical code of the physical pointer object may be used to confirm licensing or payments for the virtual medical procedure software or alignment software, and/or the correct codes may unlock a navigation software system. Values in the optical code of the physical pointer object may also be used in combination with optical codes in other medical instruments (e.g., an instrument tray, etc.) to confirm licensing or payments for the virtual medical procedure software or alignment software, and/or the correct codes may unlock a navigation software system. The data and values embedded into the optical code may be encrypted code values or data to protect keys or other valuable data in the stored data and values.

In one example, the optical code 199 may be an AprilTag, a linear barcode, a matrix two-dimensional (2D) barcode, a Quick Response (QR) code, a Fourier Tag (e.g., any optical code containing a Fourier code) or some combination thereof. An AprilTag is a two-dimensional bar code which may be a visual fiducial system useful for augmented reality and/or camera calibration. The AprilTags may be used to compute the 3D position, orientation, and identity of the tags relative to a camera, sensor, or AR headset.

During use, a spatial location of a visible anatomical feature may be recorded as identified using a tip, a pointer or other point of the physical pointer object. The spatial location may be recorded upon receiving an input into the AR headset 108 or another computer device indicating that the physical pointer object is located at or is pointing at a visible anatomical feature of the body of the person. Further, the spatial location may be defined as at least one of: a point, a curve, a traced two-dimensional (2D) area, or a traced three-dimensional (3D) shape. Accordingly, a spatial location of the physical pointer object may further define a three dimensional (3D) spatial location in X, Y and Z coordinates (or polar coordinates) as recorded using an optical sensor of the AR headset. A medical professional may provide an indicator when a curve, area or shape is starting to be traced and indicate when the curve, area or shape tracing has been completed. By knowing the location of the tag on the physical pointer object, the location of the tip (e.g., needle tip or pointer tip) can be calculated at any point in time. The image data set with the body of the person may then be aligned using the spatial location recorded for the visible anatomical feature as referenced to the virtual anatomical marker in the image data set. As a result, the image data set may be displayed using the AR headset as being visually overlaid on the body of the person.

The environment 100 may include a physical space 102 (e.g., operating theater, a lab, etc.), a user 104 (e.g. a medical professional), the patient 106, a physical pointer object 118 with an optical code 199, and an AR headset 108 in communication with a server 112 over a computer network 110. A virtual user interface 114 and a virtual cursor 122 are shown in dashed lines to indicate that these virtual elements are generated by the AR headset 108 and are viewable by the user 104 through the AR headset 108.

The image data set 116 may be captured using a non-optical imaging modality. One example of a non-optical imaging modality used to capture the image data set may be an MRI modality. In another example, the non-optical images or image data sets may be an image or image data set which includes a combination of two or more forms of non-optical imaging modality (e.g., two or more images combined together, combined segments of two or more non-optical images, a CT image fused with an MRI image, etc.). Each image data set in a separate modality may have a virtual anatomical marker in the individual image data set which may allow a PET image, a CT image, an MRI image, a fluoroscopy image, etc., to be aligned and/or referenced together with a spatial point identified by the physical pointing object on a body of a person in an AR system view.

The AR headset 108 may be an AR computing system that is capable of augmenting actual views of the patient 106 (covered by a hospital gown or fabric 107) with an image data set 116. For example, the AR headset 108 may be employed by the user 104 in order to augment actual views of the patient 106 with one or more 3D image data set views or radiologic images of the patient 106 including, but not limited to, bones (as illustrated in FIG. 1), muscles, organs, pathology such as tumors, lymph nodes or fluids 106b.

The AR headset 108 may allow an image data set 116 (or a projection of the image data set) to be dynamically reconstructed. So, as the user 104 moves around the patient 106, the sensors of the AR headset 108 determine the location of the user 104 relative to the patient 106, and the internal anatomy of the patient displayed using the image data set can be reconstructed dynamically as the user 104 chooses different orientations relative to the patient. For example, the user 104 may walk around the patient 106.

Then the AR headset 108 may augment actual views of the patient 106 with one or more acquired radiology images or image data sets (MRI, CT scan, etc.) of the patient 106, so that both the patient 106a and the image data set 116 of the patient 106a may be viewed by the user 104 from any angle (e.g., a projected image or a slice from the image data set may also be displayed). The AR headset 108 may be a modified version of the Microsoft HOLOLENS, Meta Company META 2, Epson MOVERIO, Garmin VARIA VISION, Magic Leap's MAGIC LEAP 1 or other AR headsets.

The virtual user interface 114 generated by the AR headset 108 may include options for altering the display of the projected inner anatomy of the patient 106 from the image data set 116 of the patient 106. The virtual user interface 114 may include other information that may be useful to the user 104. For example, the virtual user interface 114 may include information about the patient or the medical implements 118 (e.g., medical instruments, implants, etc.) being identified with an optical code. In another example, the virtual user interface 114 may include medical charts or other medical data about the patient 106. In some configurations, the image data 116 or captured radiological data of a person may be displayed by the AR headset 108 using a volume of the image data set 116 to display radiologically captured anatomy (e.g., bones 106b, tissue, vessels, fluids, etc.) of the patient 106a from the image data. This image data may contain axial slices, coronal slices, sagittal slices, or oblique slices of the image data. Slices may be two-dimensional (2D) slices, three-dimensional (3D) slices, and/or four dimensional (4D) slices (3D images with a time sequence of images) that have a depth as well as a height and width (e.g., one or more layers of voxels). A user 104 may control the virtual user interface 114 using: hand gestures, voice commands, eye movements, remote controls (e.g., a finger clicker), a 3D mouse, a VR wand, finger sensors, haptic technology, or other control methods.

While a distal end point or a tip distal to a handle on an elongated shaft of the physical pointer object may be used to identify the spatial location, any other pre-defined point may be used on a physical pointer object to identify the spatial location. For example, if a physical pointer object is a triangle or another polygon, then one of the points of the physical pointer object may be used as a tip which identifies a spatial location. Similarly, the physical pointer object may be a cube or other geometry and there may be multiple pointers in various sizes or colors extending from the cube or other geometry which may be used to identify a spatial location. For example, the size of the pointer or color of a pointer may correspond to a spatial point being set.

The image data set may be retrieved automatically for the body of the person using one or more optical codes on the body of the person. Alternatively, the image data set may be retrieved using the optical code on the physical pointer object, as the images needed for the medical procedure may be associated with the physical pointer object.

In one example, the patient 106 may be moved, for example, from a medical imaging room in a hospital to an operating room in the hospital. Then a user 104 (such as a medical professional in FIG. 1) may employ the AR headset 108 to determine a location of the optical code 199 on the physical pointing object 118. Next, the AR headset 108 may automatically retrieve the image data of the patient 106 based on the optical code on the physical pointing object 118.

After detecting the optical code 199 in the 3D space 102, the AR headset 108 may automatically calculate the position of physical pointing object 118. This automatic calculation may be based on: the sensed position of the optical code 199 in the 3D space 102, and/or the known fixed position of the physical pointing object relative to the position of the optical code 199.

In a further configuration, a virtual pointer or graphical pointer may be extended from and controlled by the physical pointer object and the pointer (e.g., tip) of the virtual pointer may be used to define the spatial location. The physical pointer object may be a finger of a medical professional identified by the AR headset. For example, if a finger of a medical professional is detected as a physical pointer object by the AR headset, then a virtual line or virtual object in 2D or 3D can be extended out away from the finger of the medical professional. The distal end of the virtual line or virtual object can be used as a pointer to define a location of a point, area or shape that is to be identified as the spatial location. Similarly, virtual pointer may be extended from a wand, pointer, trochar, mobile device, joystick or another physical pointer rod or pointer structure. As in the example, the virtual structure extended from the finger by identifying the finger may create a virtual ray from the finger that can be used as virtual laser pointer. This allows the medical professional to look at the anatomy that is being used at the spatial point and the medical professional can virtually touch (e.g., aim at or virtually overlay) the chosen point and register the point as a spatial location.

In an alternative configuration, the AR headset may have a virtual laser pointer without the physical pointer object where a cursor is controlled by the positioning of the user's head in the AR head set. This virtual laser pointer may allow a user to point with the virtual laser pointer. When the virtual laser pointer is in the position identifying the spatial point to be marked, a remote control or other input device (e.g., keyboard, mouse, trackball, switch, etc.) may be activated to enable the medical professional to mark one or more spatial locations. For example, the medical professional may mark fiducial 1 and/or fiducial 2. Similarly, a purely virtual laser pointer may be controlled by joystick, mouse or other input pointing control device that is not in view of the AR headset.

In one configuration, a location of an anatomical feature within a body of a person may be identified using at least two fluoroscopic (i.e., X-ray) images from a fluoroscopic imaging device. The location of an anatomical feature within a body of a person may be identified by a medical professional using a first fluoroscopic image. The fluoroscopic image is used to find the anatomical feature (e.g., the spinous process, the iliac crest, the top of the femur, etc.) because the medical professional cannot see through exterior tissue or skin. This anatomical feature may be marked in the fluoroscopic image(s). The tip of the physical pointer object may be inserted or submerged into the body of the person to touch the anatomical feature. For example, the tip of the physical image pointer may be touched to the spinous process that is underneath other tissue. One fluoroscopic image may allow the anatomical feature to be identified in the X and Y coordinate directions and then a second fluoroscopic image may be used to identify the anatomical feature in the Z direction. Accordingly, the tip of the physical pointer object can be arranged to touch the non-visible anatomical feature (which can only be seen in the fluoroscopic images) as referenced three dimensions. The tip of the physical pointer object (e.g., wand, forceps, metal sphere at the tip of a pointer, etc) can then be registered as the spatial location. In addition, the image data set may be aligned with the body of the person using the spatial location recorded for the non-visible anatomical feature as referenced to the virtual anatomical marker in the image data set (e.g., MRI image, CT scan, etc.).

This allows for identifying a location of the tip of the physical pointer object even when the tip is inside the tissue of the patient. In another configuration, a virtual needle or pointer may be generated when a visible portion of the needle or pointer is outside the body of the patient but the tip of the needle is in the body of the patient and is not visible. Since, the optical code on the physical pointer object can provide a location for the entire physical pointer object, then the tip of the needle can be projected virtually (as an overlay that simulates the tip of the needle in the patient) even though the end of the actual needle in the patient is not visible in the actual view through the AR headset. Thus, the virtual anatomical marker may be marked on the image and the location of tip of the virtual needle can be used to align or conjoin the actual view of the patient (e.g., reality) with the image data set (e.g., the captured 3D medical image).

The present technology overcomes alignment problems without the issue of markers or fiducials moving during surgery. In particular, markers or fiducials can be placed on a patient's body during surgery to assist with alignment of an image data set but when a patient's skin or other tissues are dissected or cut in surgery, then the markers or fiducials are likely to move due to the loose skin, incisions, retraction of the tissues or a change in patient position (e.g., a move between supine or prone) and displace the markers or fiducials. As a result, the present technology helps overcome this problem that may exist in the alignment methods that use: manual registration, matching curvature of the skin using mesh triangles, use of optical codes on the externalities of the body or other various tags on the body. In contrast, this technology can be used to identify a specific part of a patient's anatomy (e.g., one of the transverse processes or posterior spine processes) and the medical professional can localize to that spatial point. The identified spatial point may become a fiducial or fixed reference point for body of the patient. As described above, the image data set can be aligned to the identified spatial point using the virtual anatomical marker in the image data set. In one example, a medical professional may mark normally exposed anatomy on the body (e.g., tips of nose, tips of ears, bony prominence on a shin, temple on a head, cranial shape, iliac crest, etc.) The physical wand may then be moved by the medical professional to touch a spot, trace a virtual contour or trace a shape. For example, the physical wand can be used to trace a spatial area from the temples on a patient's head. In addition, the medical professional may mark anatomy that has been exposed during surgery and cutting of the skin open. As a result, marking may occur for a visible anatomical structure that can be seen prior to surgery or a visible anatomical structure that is only visible after surgery is underway.

To reiterate, virtual anatomical markers may be created in the image data set that are to be aligned with the spatial points identified by the physical pointer object. The virtual anatomical markers may be considered fiducials created in the image data set that can be aligned with selected spatial points. For example, a spatial point can be identified by pointing at or touching the spatial point with a wand or finger, and then the identified spatial point may be aligned with a currently selected virtual anatomical marker. Thus, a fiducial can be created in the image data set (e.g., 3D data set) and a physical fiducial point is identified on the body. This combination of aligned fiducials can create an anatomic fiducial reference system.

Figure 2:
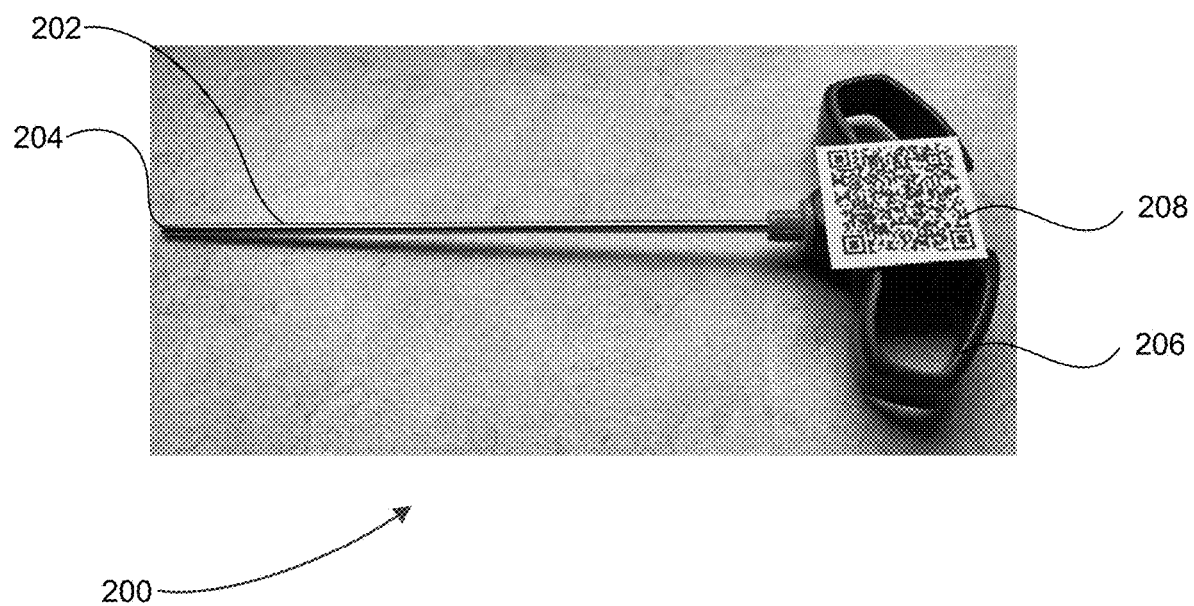
FIG. 2 illustrates an example of a physical pointer object with a 2D bar code.

FIG. 2 illustrates a physical pointer object that is a physical wand 200 or physical pointer object. The physical wand 200 may have a shaft 202 with a pointer 204 (e.g., a tip) at the end of the shaft 202. The physical wand may include a handle 206 that has loops or other structure that is convenient for the human hand to hold, as in this example. However, a handle on the physical wand may be any shape that may be held by the human hand. For example, the handle 206 may be a ball, a knob, a rod perpendicular to the shaft, a single loop or another handle type. The handle of the physical wand 200 may have an optical code 208 on the handle 206. Alternatively, the optical code 208 may be placed on the shaft of the physical wand 200 or physical pointer object. The optical code can be identified by the AR headset using an optical camera and the location of the optical code 208 may be assigned coordinates in a 3D space that the AR headset is viewing. Once the location of the optical code is known, the location and orientation of the physical wand 200 is also known because the relationship between the optical code 208 and the physical wand has been pre-defined. In addition, identifying the location of the optical code 208 allows the handle 206, the shaft 202 and then the pointer 204 or tip of the physical pointer object to be identified.

Figure 3A:
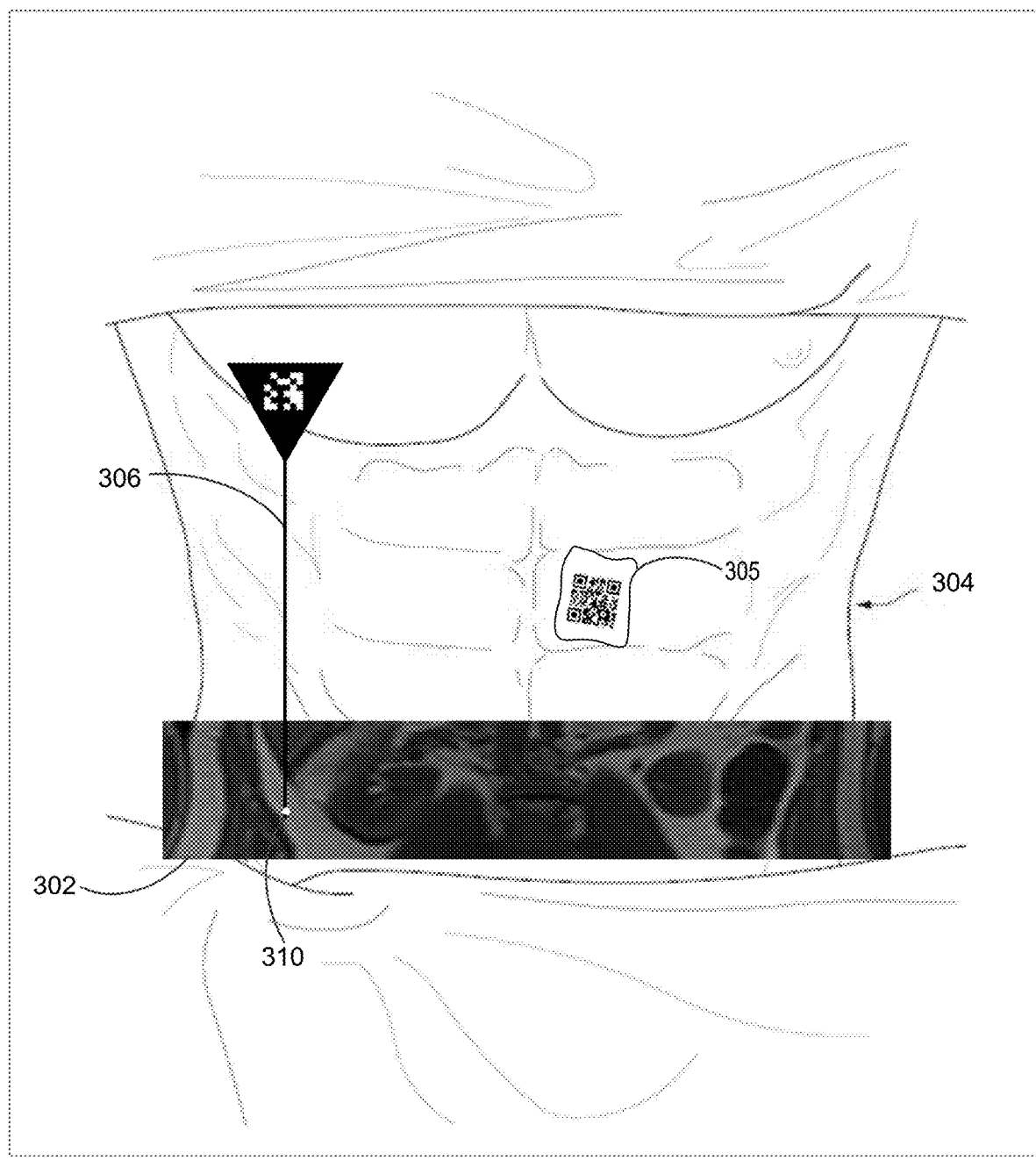
FIG. 3A illustrates an example top view of an image data set of a patient or person which may be aligned with actual views of the patient using a spatial location identified using a physical pointer object.

FIG. 3A illustrates a top view of an example of an augmented reality (AR) environment in which an image data set 302 of a patient or person 304 may be aligned with actual views of the patient using a spatial location identified using a physical pointer object 306 in a field of view of an optical sensor of the AR headset. The image data set 302 of a portion of the body of the person may be obtained using a medical imaging device, and the image data set may have a virtual anatomical marker 310 to identify an anatomical feature. In one example, the virtual anatomical marker 310 may be placed by a medical professional who marks the image with virtual marking tools (e.g., graphical marks). For example, a location for the virtual anatomical marker 310 in the image data set may be defined using a computing device or workstation controlled by a medical professional prior to a medical procedure. The virtual anatomical marker 310 in the image data set may be a virtual marker that is a dot, a line, a curve, crosshairs (see FIG. 3G), virtual marker, two-dimensional area, or a three-dimensional graphic object. A medical professional or other individual may touch a point, trace a curve or trace a shape that is to be used for alignment with a corresponding shape of a virtual anatomical marker of an image data set 302 for a patient. For example, a physical wand or virtual wand may point to one spot at a time but the medical professional may trace a contour or shape which becomes a virtual landmark that can be aligned with the virtual anatomical marker 310 in the image data set 302.

In one configuration, a physical pointer object 306 may have reflective IR (infrared) markers on or near a pointer or tip of the physical pointer object 306. The AR headset may be able to project IR light out from an AR source of the AR headset toward the physical pointer object 306. The reflection of the IR light can provide the AR headset with a specific location defined by the IR reflector. Alternatively, the physical pointer object 306 may have an IR light source that can be registered by an IR sensor of the AR headset. The strength and position of IR signal at the AR headset may be used to determine the location of the physical pointer object 306 and/or the tip or pointing structure of the physical pointer object 306.

The optical code 305 can also identify an image visible marker under the optical code that is visible in the image data set 302. The optical code 305 may be used to align the image data set 302 with the body of the patient as described in more detail in U.S. patent application Ser. No. 16/194,333 filed on Nov. 17, 2019 entitled "Using Optical Codes with Augmented Reality Displays", which is incorporated herein by reference in its entirety.

Figure 3B:
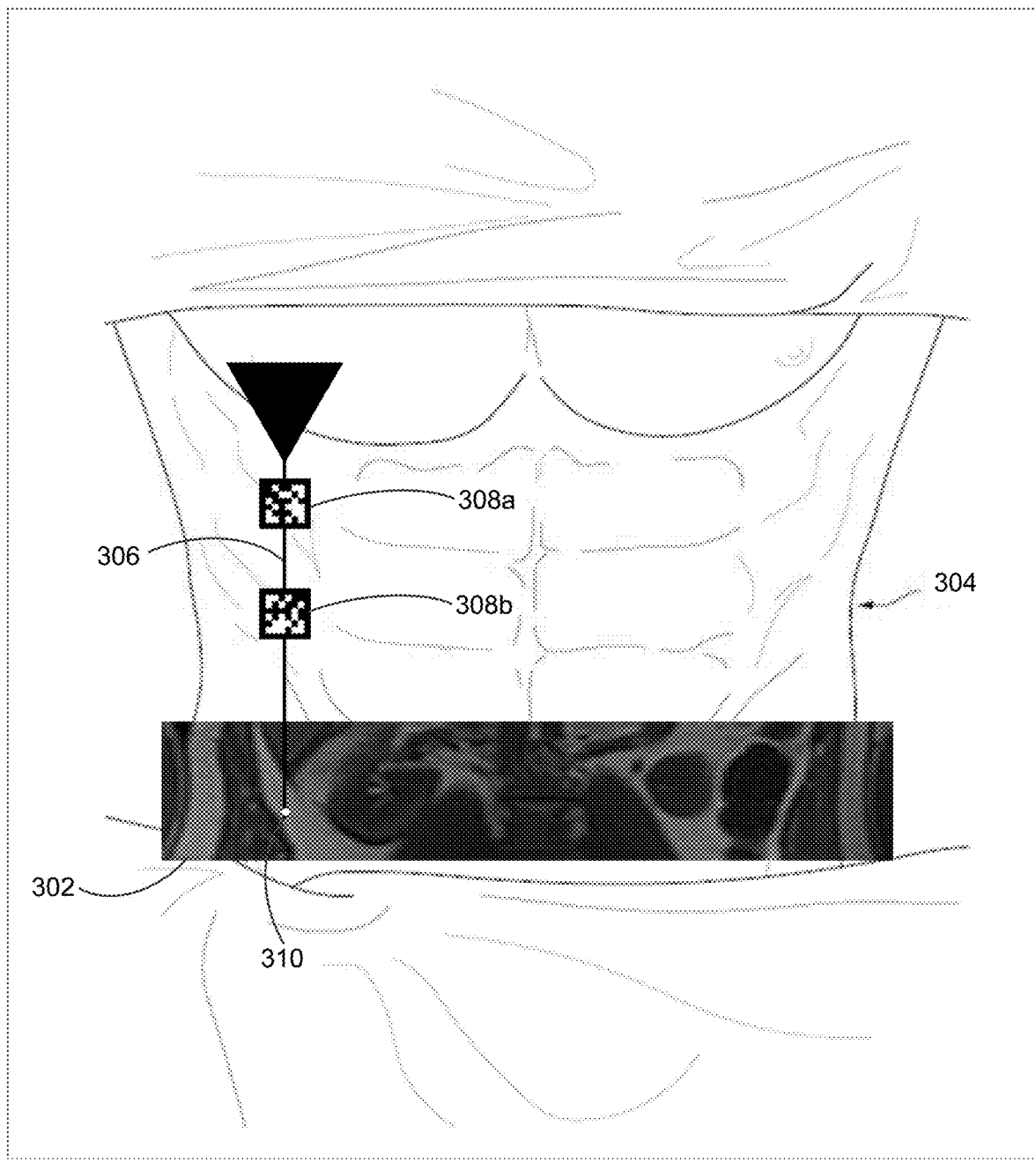
FIG. 3B illustrates an example top view of multiple optical codes used on a physical pointer object.

FIG. 3B illustrates that multiple optical codes 308a-b may be used on a physical pointer object 306. The multiple optical codes 308a-b may be used to increase the accuracy of identifying a location of the physical pointer object and/or the tip, end, pointer or pointing structure of the physical pointer object 306. The AR headset can capture the size and orientation of the optical tags 308a-b. This allows the system (e.g., AR headset) to make a better estimate of the orientation of the physical pointer object 306 (e.g., wand) in 3D space being viewed by the AR headset. In one example, a line in 3D space may be created through the center points of the optical tags 308a-b at the depth of the optical tags 308a-b attached to the physical pointer object 306. Since the length of the physical pointer object 306 is known then the tip or point of the physical pointer object can be determined.

Figure 3C:
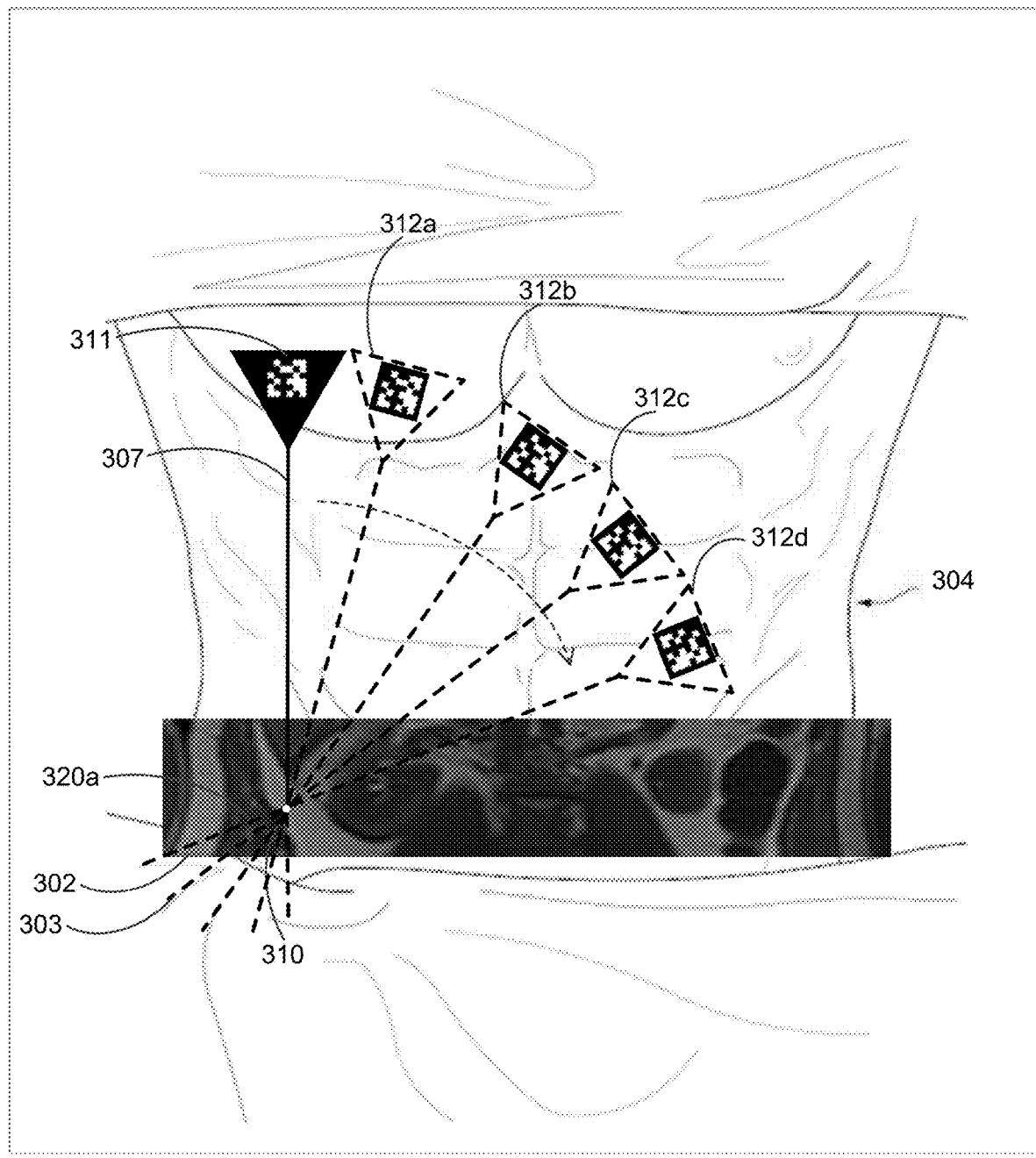
FIG. 3C illustrates an example of rotating or orbiting a physical pointer object around a point to be registered.

FIG. 3C illustrates that the accuracy of using a single physical pointer object to determine the spatial point may be further increased by orbiting, precessing, or rotating the physical pointer object 307 around the spatial point 310 that is being registered. Two or more spatial positions 312a-d of the physical pointer object 307 may be captured. The rotation of the physical pointer object may be rotated from side to side or rotated toward or away from the AR headset at any angle. The location of the physical pointer object 307 may be identified in a first position 307 using one or more optical codes 311. A virtual line may be created for each spatial orientation of the physical pointer object (e.g., multiple lines may be created for multiple spatial positions), and the lines can be used to identify the spatial point 310 to be registered. The use of two or more optical codes may create greater accuracy than just one optical code because a line may be drawn between both points to assist in finding the tip of the physical pointer object. In addition, the points delineated by the optical tags may be more accurate in the 3D space of the AR headset as the optical tags are moved left to right or up and down with respect the AR headset.

The physical pointer object may be moved to a second position 312a and a virtual a line 303 for the physical pointer object may be determined again. This movement of the physical pointer object may be repeated multiple times 312b-312d without moving the tip or point of the physical pointer object. A virtual line may be created for each spatial orientation of the physical pointer object. The virtual lines may extend through the point being registered by a defined distance or the line may infinitely extend out through the point to be registered. Each time after the physical pointer object 307 is rotated with respect to the location where the physical pointer object is in contact with on the human patient's body, a new virtual line may be computed for that spatial position of the physical pointer object 307.

The multiple virtual lines may have a virtual intersection point or a best fit (e.g., an approximate) intersection point computed for the group of lines. The virtual intersection point or approximated virtual intersection point may be considered the spatial point the medical professional wants to register and the spatial point that is to be aligned with the virtual anatomical marker 310. The intersection (or nearest approximation of the intersection) of the virtual lines may then be calculated and is then determined to be the spatial point. Thus, the spatial point may be more accurately identified using multiple positions of the physical pointer object and virtual lines to identify the spatial point. Capturing multiple positions for the physical pointer object can overcome problems with variances in positioning the physical pointer object with respect to the AR headset (e.g., it will not matter whether the physical pointer object is initially positioned too far away, too much to the right or left, etc.).

While a higher precision location can be more correctly determined using virtual lines generated when the optical tags are moved side to side or up and down with respect to the AR headset, the optical tags 311 tend to be less accurate in the depth direction from the AR headset. Detecting where an optical code is located in depth is performed in part by the size of the optical code but this has some limitations in terms of depth resolution. One reason for these limitations is that computing the depth of an optical code from the AR headset may use the size of the tag but if the image recognition software is off by a fraction of a pixel due to lighting or other issues, then the registration of the tip of the physical pointer object or wand may be off by millimeters, and this may cause problems in a medical or other engineering settings. While the spatial point may be identified using the physical pointer object in a single position or multiple positions using virtual lines, any error that introduced through the optical codes, lighting, AR headset, optics, or computing system when identifying the optical codes may result in a spatial point that is less accurate. As a result, virtual planes (described below) can be used to correct such depth problems.

Figure 3D:
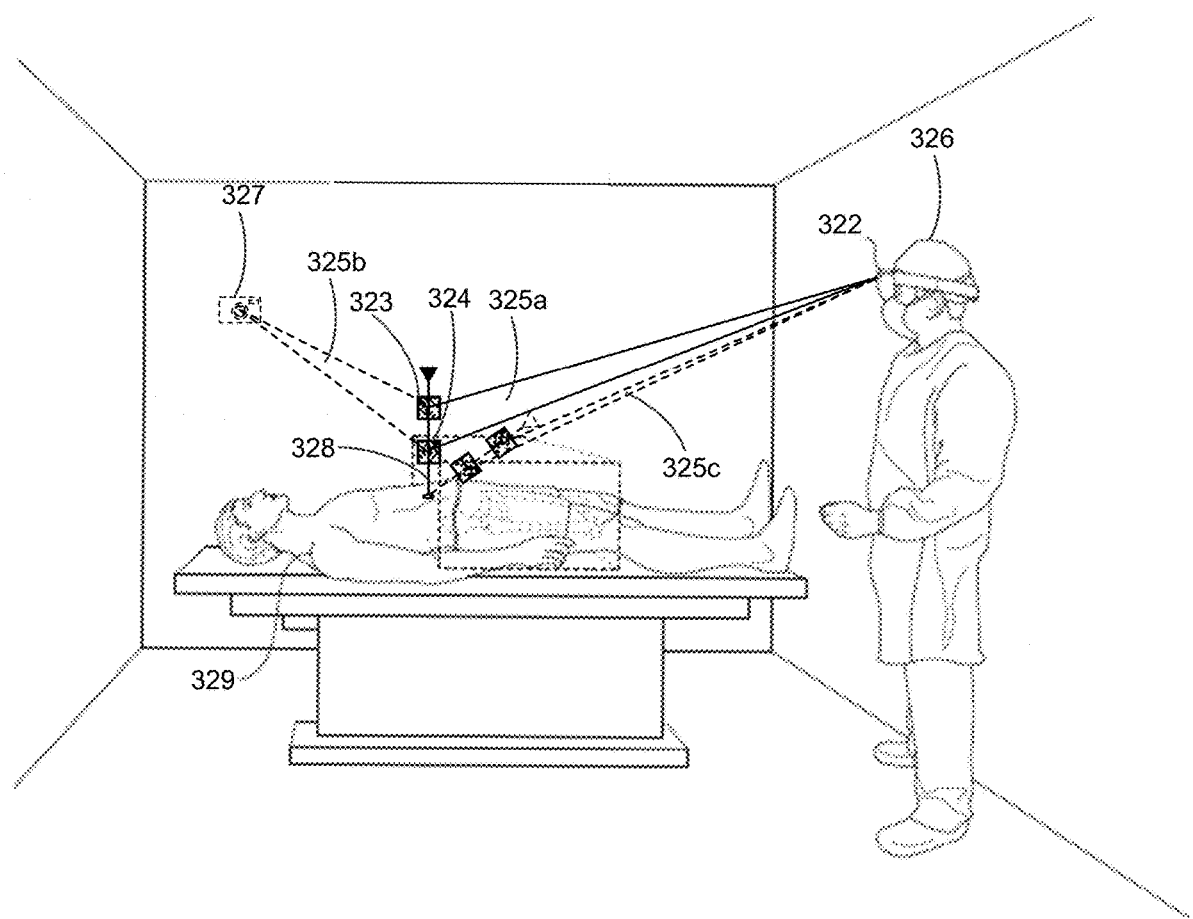
FIG. 3D illustrates an example of virtual planes that may be formed using a physical pointer object and a camera on the AR headset.

FIG. 3D illustrates an example of planes that may be formed using optical codes on a physical pointer object viewed from multiple angles or in multiple spatial positions and a location of a camera on the AR headset. To form a plane, at least three points are needed in the 3D space of the AR headset. At least three points can be determined accurately. One of these points is the 3D position of a camera 322 in an AR headset (e.g., in the middle of the medical professional's forehead). In addition, the 3D position of the optical codes can be accurately determined in the X, Y and Z coordinates but the optical codes location's depth is not as accurate in depth (e.g., the Z direction). Accordingly, a 3D plane 325a can be computed using those three points. Even if the depths of the points from the optical codes are not quite accurate (off by millimeters), the plane 325a is still the same because the points of the optical codes will still be in the plane but will simply be farther away in the plane. Using a plane to find the spatial point is much more accurate than using lines alone. The position of the camera 322 in the AR headset is already known. The second two points of the plane are points on each of two optical codes. The centers (or other points) of the optical codes may be used as two additional points in the plane 325 being created. The plane may extend infinitely out from the plane created by the three points used to define the plane (even though a finite triangular plane is used to illustrate the three points used to form the plane in FIG. 3D).

The medical professional creating the planes and/or holding the physical pointer object in contact with a patient 329 may be looking at the edge of the plane and the infinite plane may pass thorough or bisect the medical professional in an edgewise orientation. A medical professional may look at the physical pointer object 328 from multiple angles as illustrated by the second camera 327 to create multiple planes with the optical codes on the physical pointer object. In addition, a medical professional may move the physical pointer object 328 from side to side through varying degrees of rotation (e.g., 20 to 90 degrees different than an initial plane) in order to create multiple different planes. These planes can intersect at the pivot point for the physical pointer object which is on the anatomical feature of the patient 328 (e.g., on the skin, on a bone during an operation, or another anatomical feature).

FIG. 3D illustrates two other planes 325b-c that are created when the medical profession views the physical pointer object from another vantage point or the physical pointer object is rotated about a point. Computing the intersection of three or more planes 325a-c results in a spatial point that can be aligned to a virtual anatomical marker in the image data set with the patient's body. At least three planes are used to calculate the spatial point but more planes may increase the accuracy of the spatial point registration. On the other hand, two virtual lines created from the physical pointer objects may identify the spatial point.

Using the planes of the present technology, the spacing between the optical codes and the length of the physical pointer object does not need to be known. Instead, the three known points are formed into a plane regardless of the distance between the points. The medical professional viewing the physical pointer object can create 20 to 30 planes and then the intersection operation may be performed. The intersection operation may use an optimization computation to compute the plane intersection point (e.g., usable spatial point) that is the shortest distance from all the planes.

In one configuration, the spatial point may be found by first calculating the spatial point with one or two lines obtained using the physical pointer object and that is a good initial measurement. Then a few minutes later when enough planes have been captured, a more accurate spatial point may be calculated and registered. The use of at least three or more planes that are oriented at a substantial angle from each other increases the accuracy of the intersection. Planes that are only a few degrees apart are less accurate because such planes may be too close to parallel to each other to provide a highly accurate intersection. When planes are used that are 20 to 90 degrees apart in their relative angle then a more accurate intersection can be computed. Ideally the planes will intersect at one point but a best fit computation may be performed to determine a spatial point even when an ideal intersection is not available. In one example, the measurement accuracy or registration of the spatial point in the 3D space viewed by the AR headset as found by using the planes may be made to a tenth of a millimeter or even less.

The use of planes helps correct for the reduced accuracy of determining the depth of the optical codes with respect to the AR headset or in the 3D space. Optical codes may appear to be larger or smaller depending on the amount of light that is reflected off the optical code. This is because the computer vision process may use a threshold to find a border between the black and white. If the room is brighter, than the brighter area overpowers the darker area due to the thresholding process. This may result in a fraction of a pixel of change in apparent size. As a result, the optical code may appear to be a millimeter larger or smaller depending on how much light is hitting the optical code. A millimeter of size difference for an optical code may register in the system as a depth difference of a centimeter, which may result in measurement inaccuracies in the registration of the spatial point. The lighting on an optical code is difficult to control in an operating room or other scenarios and so relying on the depth of the code may be less useful. However, the center of the optical tag can be computed in an accurate and angle insensitive way by computing a ray from the AR camera through center of the optical tag. Using the planes to find the spatial point can correct for significant error in the depth of the optical tags. Any optical tags moved along the ray from the AR camera will still be in the same plane defined by the optical tags and the location of the AR camera. Thus, using the planes makes the spatial point computation more insensitive to the depth of the optical codes.

Figure 3E:
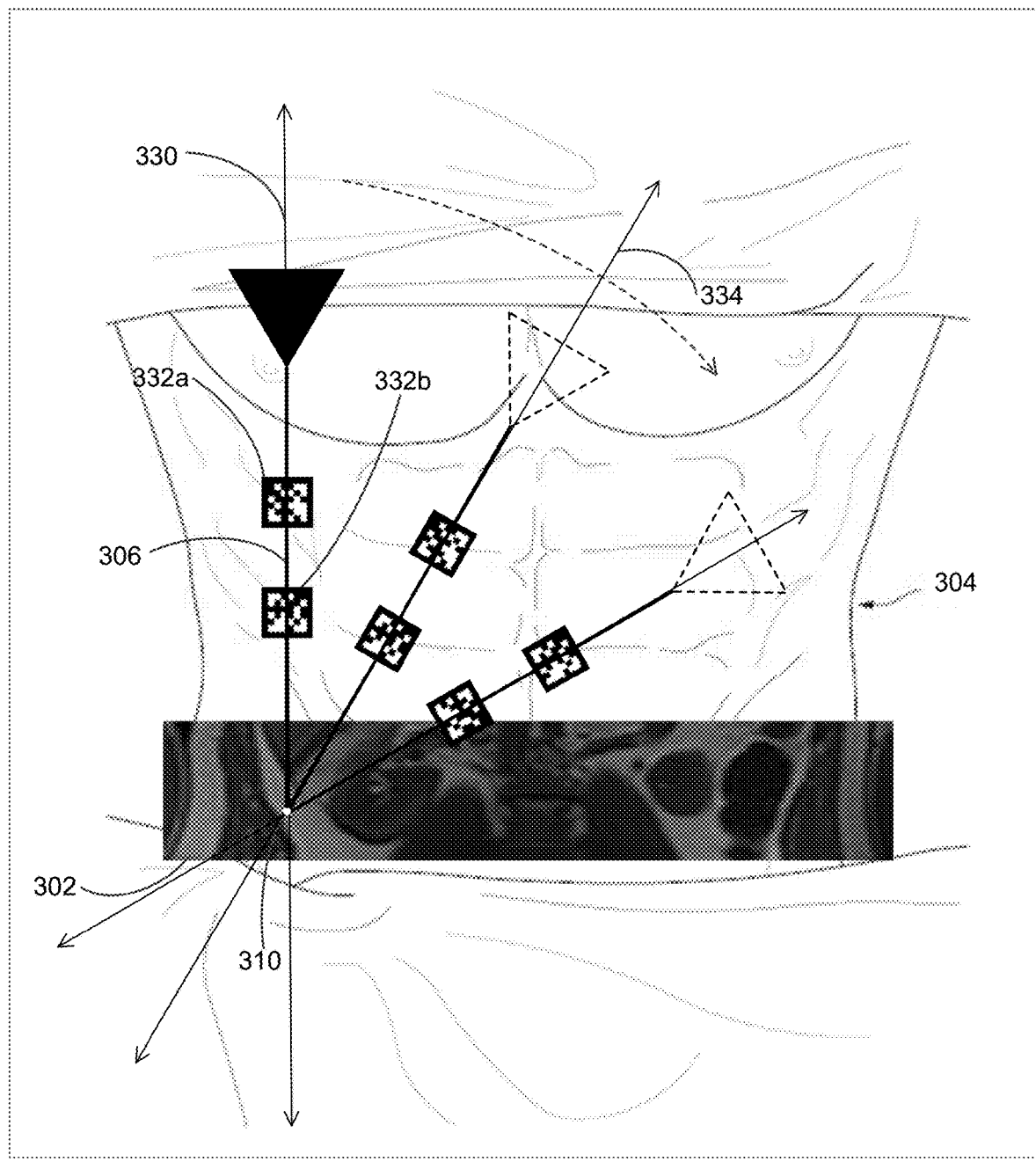
FIG. 3E illustrates an example of creating virtual planes using a physical pointer object.

FIG. 3E illustrates a first virtual pointer plane 330. This first virtual pointer plane 330 may be created using the AR camera location and the one or more optical codes 332a-b on the physical pointer object 306. The planes from FIG. 3E are seen from the edge as the planes would be viewed from the medical professional's view or AR headset camera's point of view. The AR headset camera would be above FIG. 3E. The first virtual plane 330 may be created with a point from AR headset camera and points from the optical code(s), and the plane may pass through the optical codes, the pointing structure 306 (e.g., rod in this case) and the overall physical pointing object.

A second virtual plane 334 may be created when the physical pointer object 306 is rotated or orbited around the point 310 being touched by the physical pointer object 306. An intersection between the three or more planes can be used to identify the spatial point that is being selected by the medical professional. The physical pointing device 306 may be placed in any number of rotated or orbiting positions around the point on the patient 304 being touched by the medical professional, and a virtual pointer plane may be generated for each of the multiple spatial positions of the physical pointing device. For example, the physical pointing device may be oriented at any number of different degrees (any orientation of 0 to 360 degrees in multiple axes around the point) with respect to the spatial point to be identified or selected.

Figure 3F:
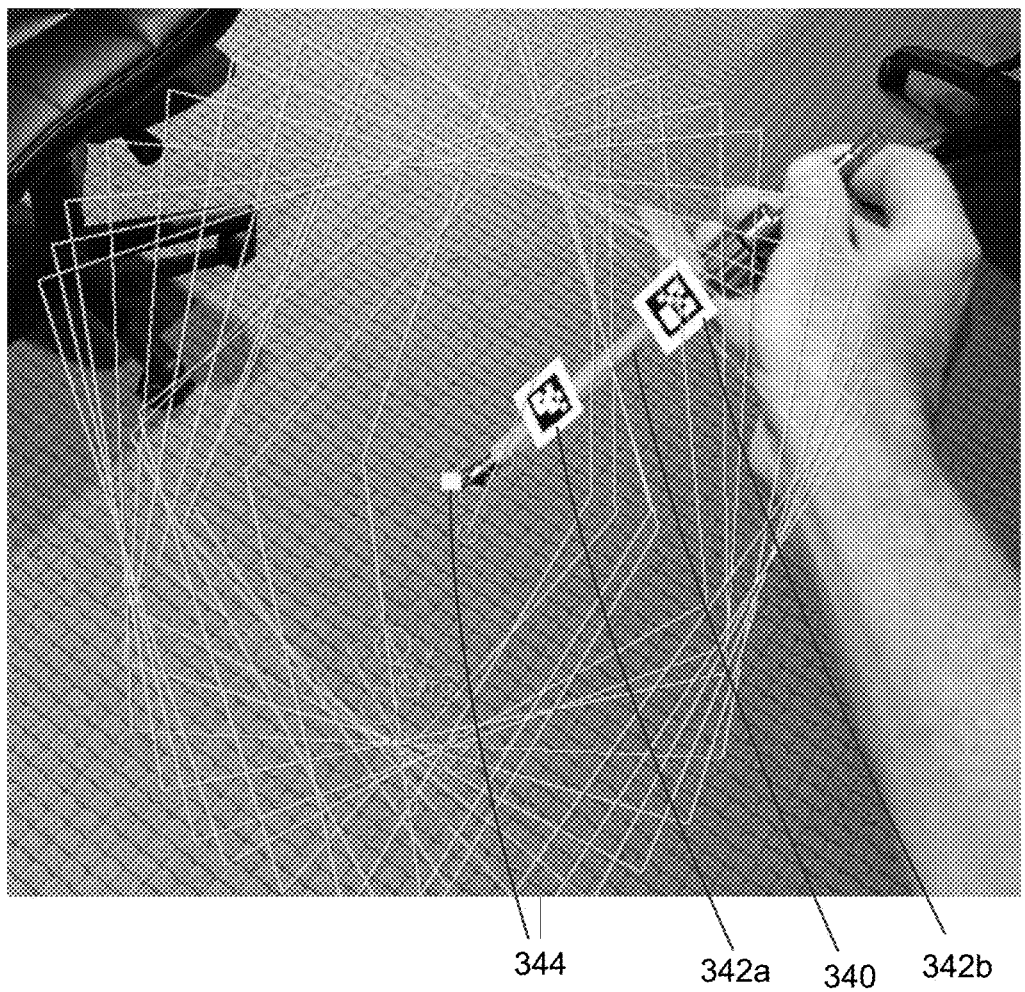
FIG. 3F illustrates an example of a physical pointing device being rotated around a point and multiple planes are generated to be used for registering a spatial point.

FIG. 3F illustrates an example of a physical pointing device 340 with two optical codes 342a-b being rotated around a point and multiple virtual pointer planes are generated using the known location of the camera in the AR headset and a point in each of the optical codes 342a-b. The multiple virtual pointer planes are then used to generate the spatial point 344 which is being registered or selected. The three or more virtual pointer planes may intersect each other at the point in space being registered or selected, and the virtual pointer planes can be used to calculate the spatial point 344. The generation of the planes may be triggered automatically as the physical pointing device is moved (e.g., at intervals of time) or only upon explicit input from a medical professional when the physical pointing device is in a desired orientation. The virtual pointer plane may pass through the physical pointing object and extend out infinitely up, down, away from and through the AR headset wearer in order to create a mathematical intersection of the planes. In other words, the plane can be a mathematically infinite plane or the planes may be large enough to provide the needed plane intersections.

Figure 3G:
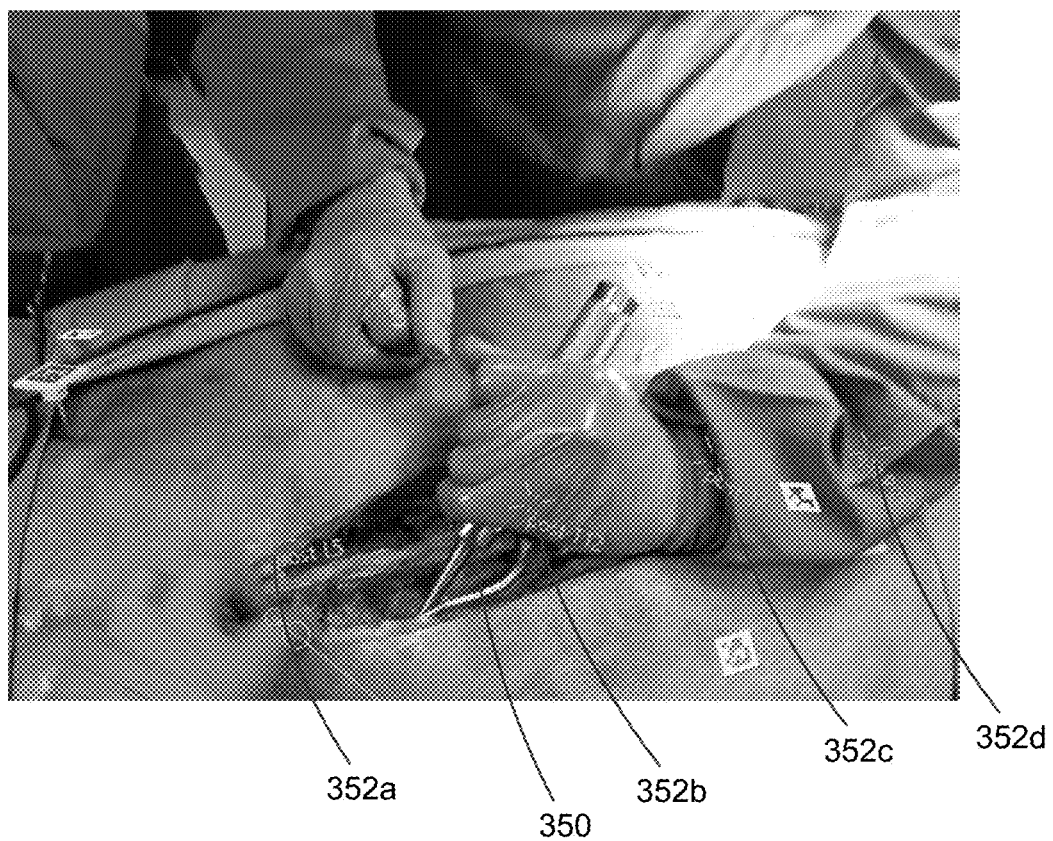
FIG. 3G illustrates an example of a physical pointing device pointing to physical anatomical point beneath the skin of a patient's body.
Figure 3H:
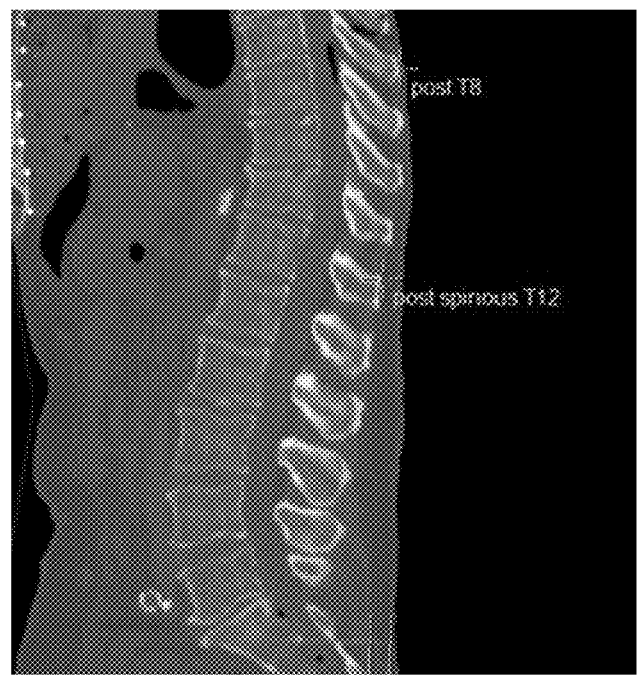
FIG. 3H and FIG. 3I illustrate fiducial points or anatomical points marked on two dimensional and three-dimensional image data sets.
Figure 3I:
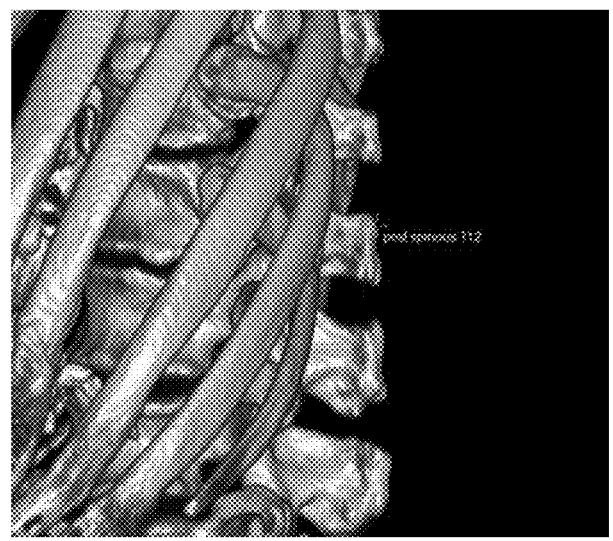

FIG. 3G illustrates an example of a physical pointing device 350 that is pointing to physical anatomy beneath the skin of the patient's body. FIG. 3G further illustrates spatial points or internal fiducial points 352a-c (e.g., L5, T12, T8, T4) that have been registered using the physical pointing device 350. FIG. 3H illustrates virtual anatomical markers or fiducial points that have been marked on an image data set (e.g., T8 and T12) and are illustrated in a two-dimensional view of an image data set. FIG. 3I illustrates a virtual anatomical marker or a fiducial point that is illustrated in FIG. 3H (e.g., the posterior spinous process of T12) and is marked in a three-dimensional view of an image data set.

In one example of a method used with elements described in FIGS. 3C through 3I, the operation of identifying a spatial location using a virtual plane (or a virtual line) may include operations to find the spatial point. In one operation, a first virtual plane for the physical pointer object in a first spatial orientation may be generated. The virtual plane may be an extension of the physical pointer object or a virtual object to assist with finding the spatial point. For example, the virtual plane may be a plane formed using a point defined by a camera in the AR headset and points from the optical codes on or associated with the physical pointer object.

Figure 4A:
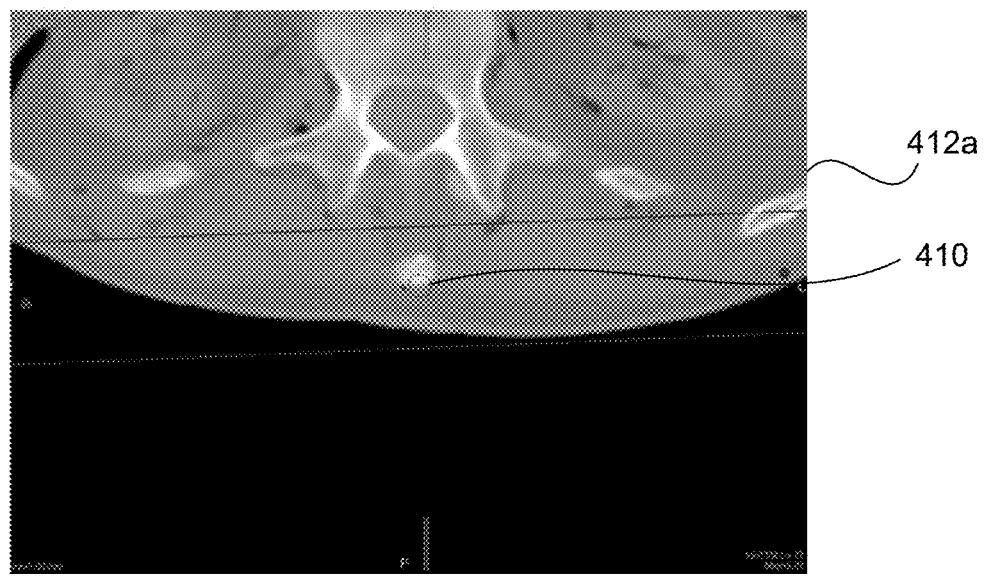
FIG. 4A illustrates an example of a cross-sectional view of location on a vertebra of a person's body where a virtual anatomical marker has been created by a medical professional.

Another operation may be generating a second virtual plane and a third virtual plane (or second virtual line and third virtual line) for the physical pointer device in a second spatial orientation. Once at least three virtual planes (or two virtual lines) exist, then an intersection of the first virtual plane, second virtual plane and third virtual plane can be calculated. The intersection of the three virtual planes define the spatial location. In the case of virtual lines, at least two lines are generally used to identify the spatial point. This process may also be performed with many virtual planes. For example, 20 spatial positions of the physical pointer object may be captured and then the virtual intersection of the virtual planes for each spatial position may be calculated to find the spatial location to register. FIG. 4A illustrates a cross-sectional view of a location on a vertebra of a person's body where a virtual anatomical marker 410 has been created by a medical professional to identify a location in the image data set 412a, which may be aligned with the spatial location identified by the physical pointer object. For example, the virtual anatomical marker 410 may be a colored green circle in the image data set.

Figure 4B:
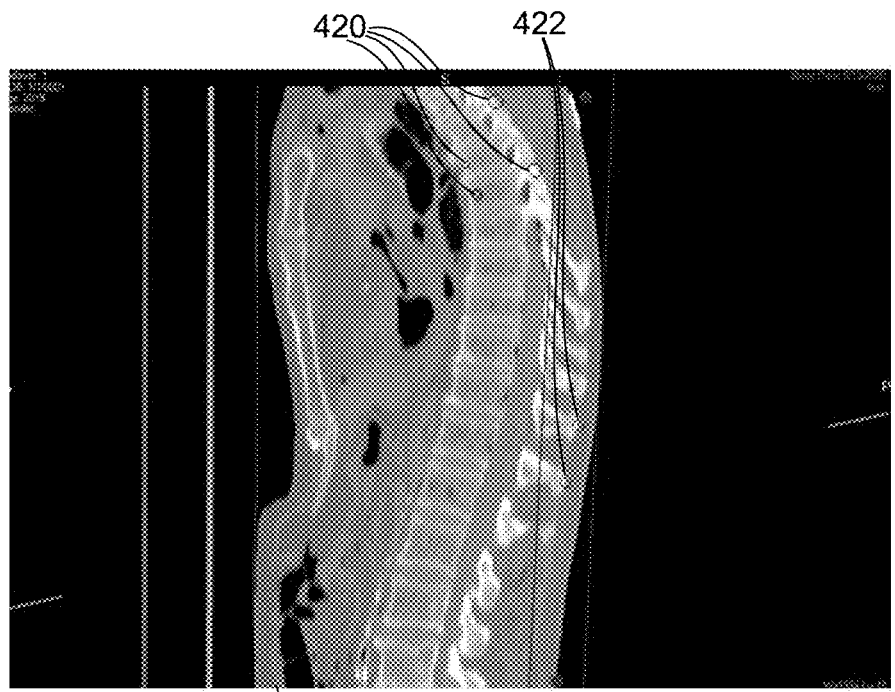
FIG. 4B illustrates an example cross-sectional side view of locations in a person's spinal area with virtual anatomical markers.

FIG. 4B illustrates a side view of locations in a person's spinal area where virtual anatomical markers 422 have been made by a medical professional to identify a location in the image data set 412b that may be aligned with the spatial location identified by the physical pointer object. In addition, red circles 420 can be seen where a pedicle screw tracks during a medical procedure.

Figure 4C:
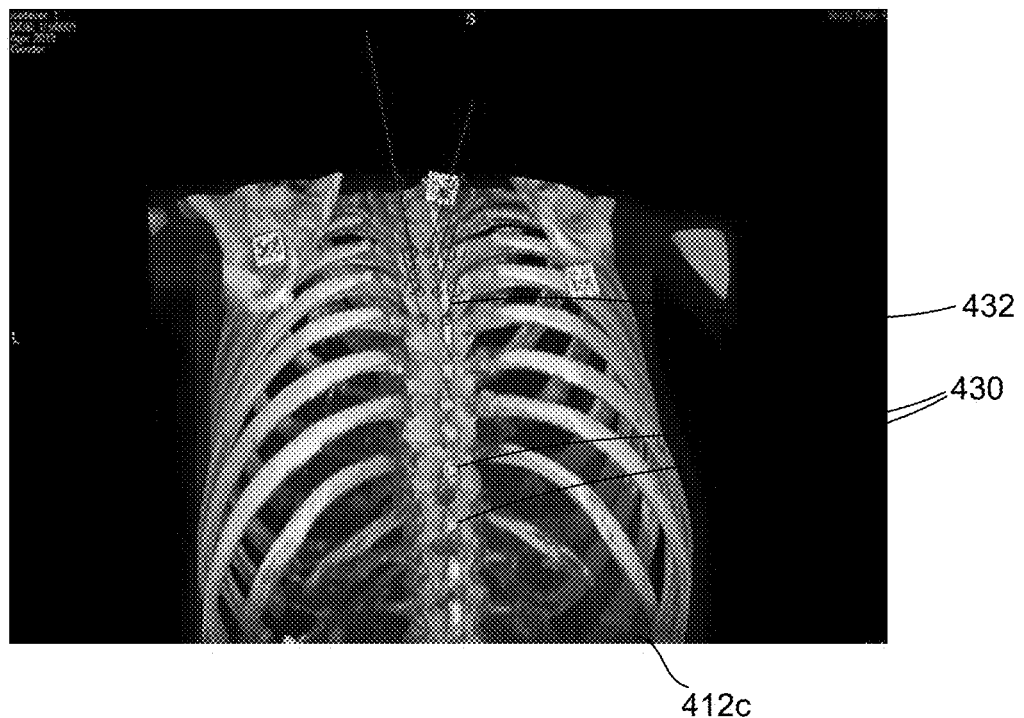
FIG. 4C illustrates an example posterior view of locations in a person's spinal area with virtual anatomical markers.

FIG. 4C illustrates a back view of locations in a person's spinal area where virtual anatomical markers 430 have been made by a medical professional to identify a location in the image data set 412c that may be aligned with the spatial location identified by the physical pointer object. Additional markers 432 are illustrated to show where alignment tools and pedicle screws are to be applied during a medical procedure.

The process of aligning an image data set with a body of a patient using a spatial point identified by a physical pointer object may be a multi-step process. An image data set that is a 3D image or multi-planar image may be viewed on a workstation as a 3D image or a multi-planar image. The image data set may have been previously captured using a desired imaging modality (MM, CT Scan, etc.) The medical professional viewing the image data set may select and mark one or more virtual anatomical markers (e.g., fiducial reference points). These virtual anatomical marks reference anatomic structures that a doctor can identify in a medical procedure (e.g., a surgery). These markings in the 3D image set may be marked using a point, a circle, a box, a 2D plane, a virtual 3D object, etc.

The image data sets can be viewed as 3D images and become image overlays in the AR headset. An image data set may be called a holographic image when viewed through the AR headset, and the image data set may be aligned to the patient. The alignment may take place using the virtual anatomical marker and a spatial point defined by a physical pointer object. The image data set can be projected onto the patient and viewed using the AR headset.

Figure 5:
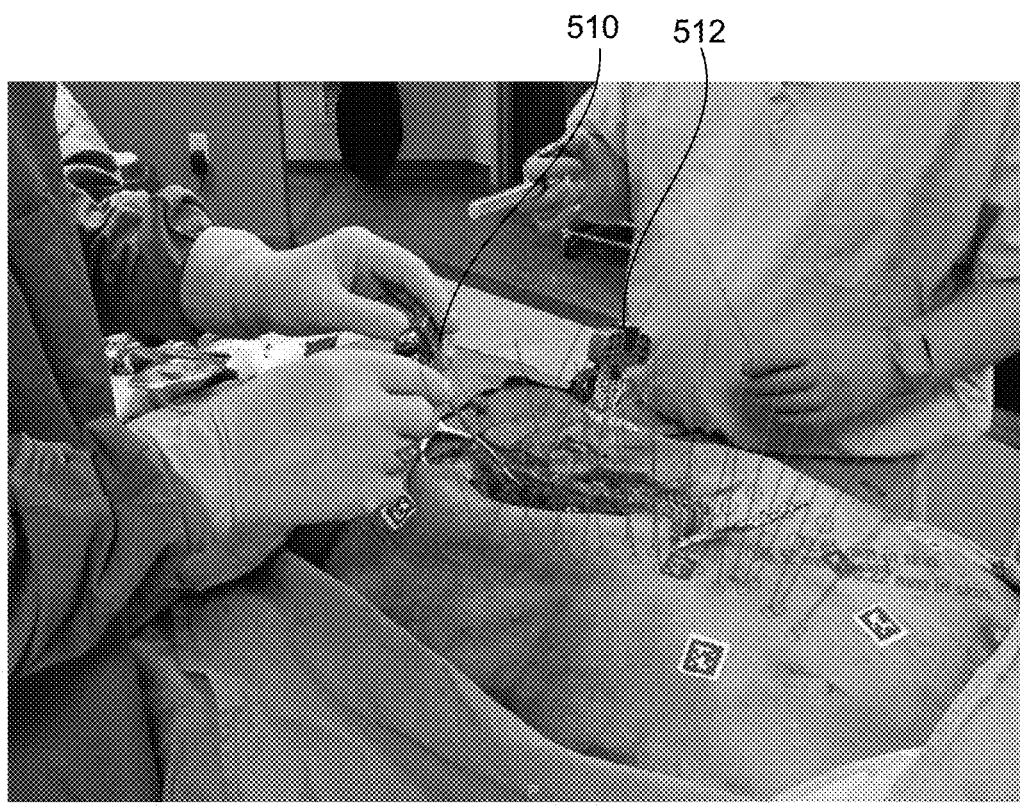
FIG. 5 illustrates an example use of a physical pointing object to enable alignment of virtual anatomical markers made by a medical professional in an image data set to spatial locations identified by the physical pointer object.

FIG. 5 illustrates identifying a spatial location identified by the physical pointer object 510. The physical pointer object 510 may have an optical code on the physical pointing object as illustrated by the physical wand 512 to the side of person's body (cadaver shown). In this example, the spine may be exposed and then a medical professional or viewer may see the spinous process. The medical professional can move the physical wand, needle, or physical pointer object, and an optical code on the physical wand may be registered by the AR headset. The optical code can be fixed to the physical wand. This registration of the physical pointer object enables the AR headset to identify where a pointer or tip of the wand or needle is located in 3D space in front of the AR headset. Then the spatial location identified using the physical pointer object can be aligned with a virtual anatomical marker of an image data set.

This technology may improve alignment as compared to prior existing alignment methods which use: manual alignment, skin or body contour alignment, alignment using optical codes on the patient, or image visible markers associated with optical codes on the body of the patient. In this alignment technology, the virtual anatomic markers are used as fiducials (e.g., a virtual tag) in the image data set and the virtual anatomic markers can be aligned with a point, curve, area or structure that can be actually be seen through the AR headset. The spatial location (e.g., physical spot) to be aligned with an image data set can be quickly specified with a high degree of three-dimensional accuracy as compared to prior methods due to using a physical wand, needle, trocar, virtual wand, virtual laser pointer or another physical or virtual pointer.

Figure 6:
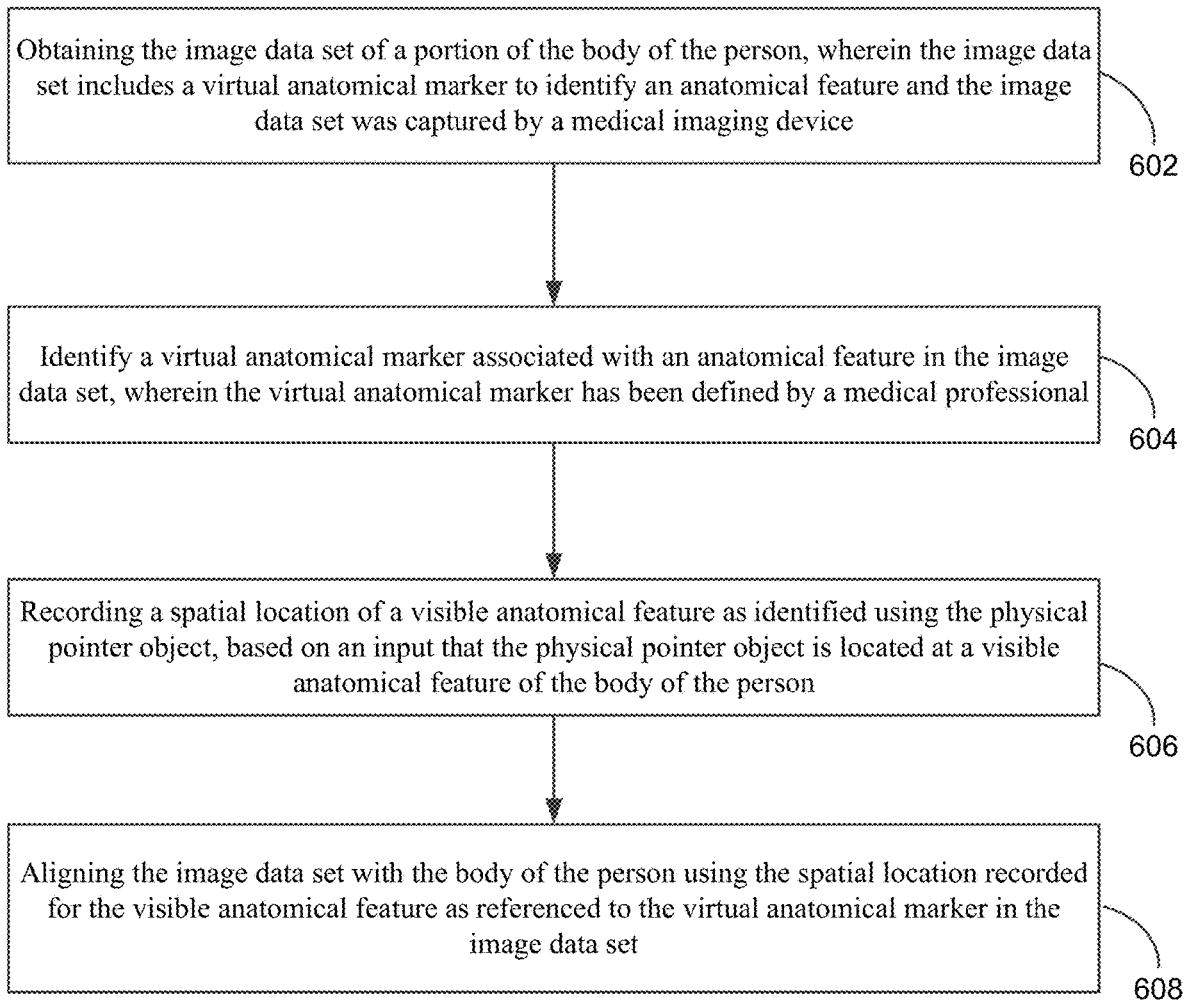
FIG. 6 is flow chart of an example method for using an augmented reality (AR) headset to co-localize an image data set with a body of a person using a physical pointer object.

FIG. 6 illustrates a method for using an augmented reality (AR) headset to co-localize an image data set with a body of a person. One operation may be obtaining the image data set of a portion of the body of the person, as in block 610. The image data set may include a virtual anatomical marker to identify an anatomical feature and the image data set may be captured by a medical imaging device. The virtual anatomical marker may be created or marked by a doctor or another medical professional using a separate computing device or workstation.

Another operation may be identifying a spatial location of a physical pointer object in a field of view of an optical sensor of the AR headset, as in block 604. An optical code on the physical pointer object may enable the AR headset to determine the spatial location of the physical pointer object. Alternatively, the location of the physical pointer object may be determined by detecting the edges of the physical pointer object using known edge and object detection processes. For example, the spatial location of the physical pointer object may be a three-dimensional (3D) location detected by the optical sensor of the AR headset. The physical pointer object may be a physical wand, a needle, a trocar or a physical object with a pointing tip or pointing edge. The physical pointer object may also be a finger of a person or medical professional identified by the AR headset.

A spatial location of a visible anatomical feature as identified using the physical pointer object may be recorded. The spatial location may be identified using a pointer (e.g., a tip) or marked point on the physical pointer object. The registration of the spatial location may be initiated based on an input (e.g., a keyboard, a mouse click, a foot pedal activation, hand signal to the AR headset, voice command or another input) that a pointer or tip of the physical pointer object is located at portions least a portion of a visible anatomical feature of the body of the person, as in block 606. The spatial location may be a point, a traced curve or other traced shape (e.g., in 2D or 3D).

The image data set may be aligned with the body of the person using the spatial location recorded for the visible anatomical feature as referenced to the virtual anatomical marker in the image data set, as in block 608. For example, the virtual anatomical marker may be set to be at the same 3D location as the spatial location or any offset from the spatial location. In addition, the image data set may be visually overlaid on the body of the person using the AR headset.

Figure 7:
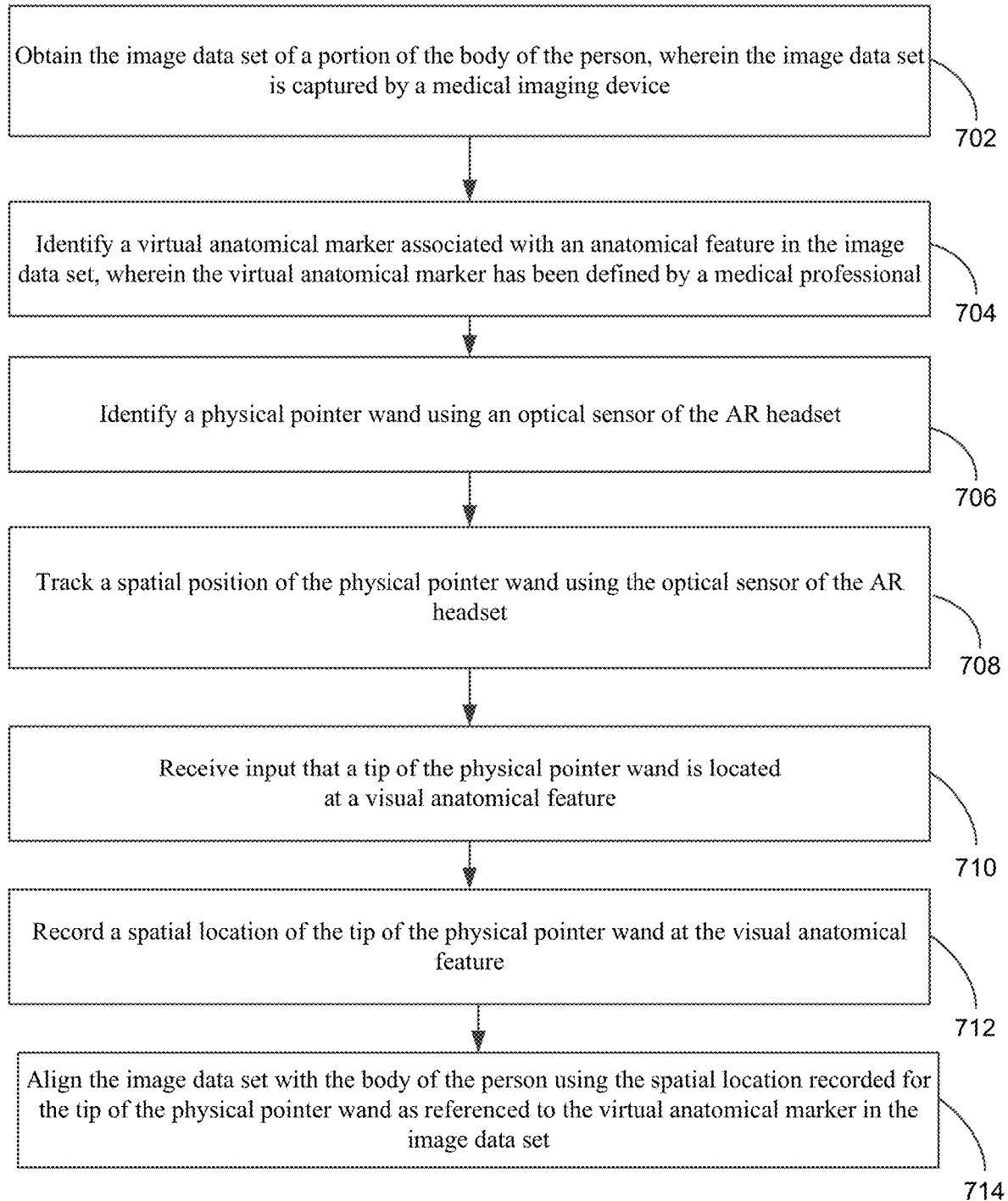
FIG. 7 illustrates a method for using an augmented reality (AR) headset to co-localize an image data set with a body of a person using a physical pointer wand.

FIG. 7 illustrates a method for using an augmented reality (AR) headset to co-localize an image data set with a body of a person. The method may be implemented using at least one processor and at least one memory device including a data store to store a plurality of data and instructions that, when executed, cause the system to perform the method. A first operation may be to obtain the image data set of a portion of the body of the person, as in step 702. The image data set may be captured by a medical imaging device.

Another operation is to identify a virtual anatomical marker associated with an anatomical feature in the image data set, as in block 704. The virtual anatomical marker may be defined by a medical professional prior to a medical procedure. In addition, a physical pointer wand may be identified using an optical sensor of the AR headset, as in block 706. The physical pointer wand may have an optical code on the physical wand to enable recognition of the physical pointer wand. The spatial position (e.g., spatial coordinates) of the tip or pointer of the physical pointer wand may be determined by referencing the optical code.

A spatial position of the physical pointer wand may be tracked using the optical sensor of the AR headset, as in block 708. Input may be received that a tip of the physical pointer wand is located at a visual anatomical feature, as in block 710. For example, a button may be pressed or sensor (optical eye) may be trigger to denote that the physical pointer wand is at the desired spatial location. A spatial location of the tip of the physical pointer wand at the visual anatomical feature may be recorded as in block 712. The image data set may then be aligned with the body of the person using the spatial location recorded for the tip of the physical pointer wand as referenced to the virtual anatomical marker in the image data set, as in block 714. This alignment occurs in the AR headset for the viewer using the AR headset.

In one configuration, a virtual pointer or graphical point extension may be extended from and controlled by the physical pointer object, and the tip of the virtual pointer may define the spatial location. The virtual pointer may be graphically generated by the AR headset and the virtual pointer may be aligned with and/or controlled by one or more axes or points of the physical pointer object. For example, the virtual pointer may be aligned with the lengthwise axis of a shaft of a physical pointer object.

Figure 8:
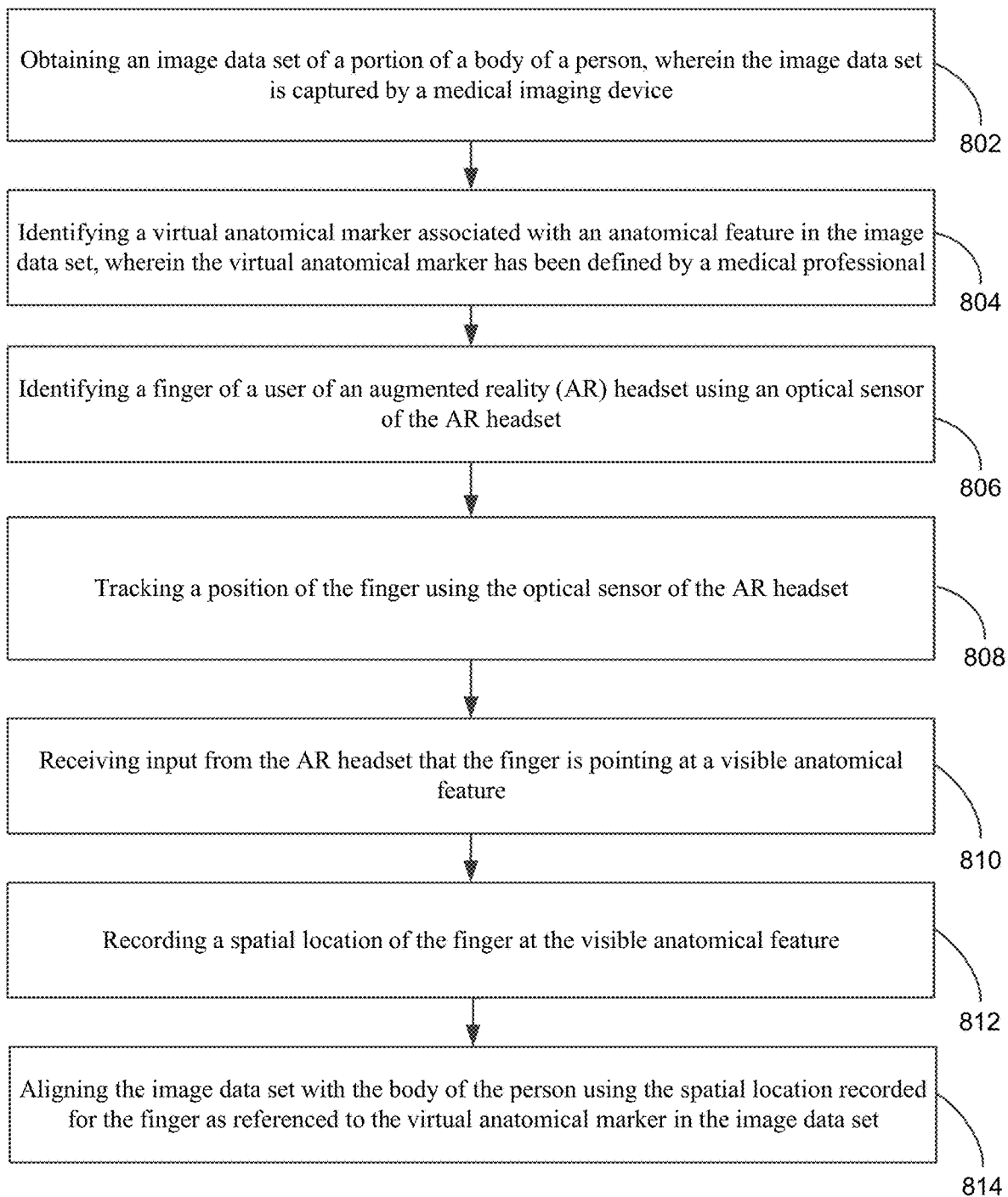
FIG. 8 illustrates a method for using an augmented reality (AR) headset to co-localize an image data set with a body of a person using a finger as a physical pointer object.

FIG. 8 illustrates the use of a finger of a user as a physical pointing object. A first operation may be obtaining an image data set of a portion of a body of a person, wherein the image data set is captured by a medical imaging device, as in block 802. A virtual anatomical marker associated with an anatomical feature in the image data set may be identified, as in block 804. The virtual anatomical marker can be defined by a medical professional prior to a medical procedure (or even during a medical procedure) using a separate computing device.

A finger of a user of an augmented reality (AR) headset may be identified using an optical sensor of the AR headset, as in block 806. A position of the finger may be tracked using the optical sensor of the AR headset, as in block 808. Input may be received at the AR headset that the finger is pointing at a visible anatomical feature, as in block 810. Further, a spatial location of the finger at the visible anatomical feature may be recorded. The image data set may then be aligned with the body of the person using the spatial location recorded for the tip of the finger as referenced to the virtual anatomical marker in the image data set.

As described with respect to a physical pointer object or a wand, a virtual pointer may be extended from the finger of the user and may be viewable through the AR headset. The virtual pointer may be a graphical pointer extended from the finger by the AR headset. The tip of the virtual pointer (or an end of the graphical pointer) may be used to identify the spatial location. In one implementation, the finger may have an optical code on the finger to enable recognition of the finger.

As discussed earlier, the ability to align the image data set with anatomical structures in a body of a patient is valuable when performing many actions in a medical procedure. If the image data set does not line up closely to the anatomical structure or actual human tissue that was previously imaged, then the image data set is less useful in a medical procedure situation. For example, if the image data set that represents human tissue (e.g., an imaged hole in a skull) does not line up with the actual human tissue (e.g., a real hole in the skull) then the image data set is much less useful in a medical procedure. In some cases, a coarsely aligned image set may be useful for simulation or practice purposes but not for a surgical procedure. In contrast, the present technology enables alignment of an image data set for an MRI, CT or PET scan data set with a degree of resolution that can allow medical personnel to use the image data set in a high precision medical procedure.

Figure 9:
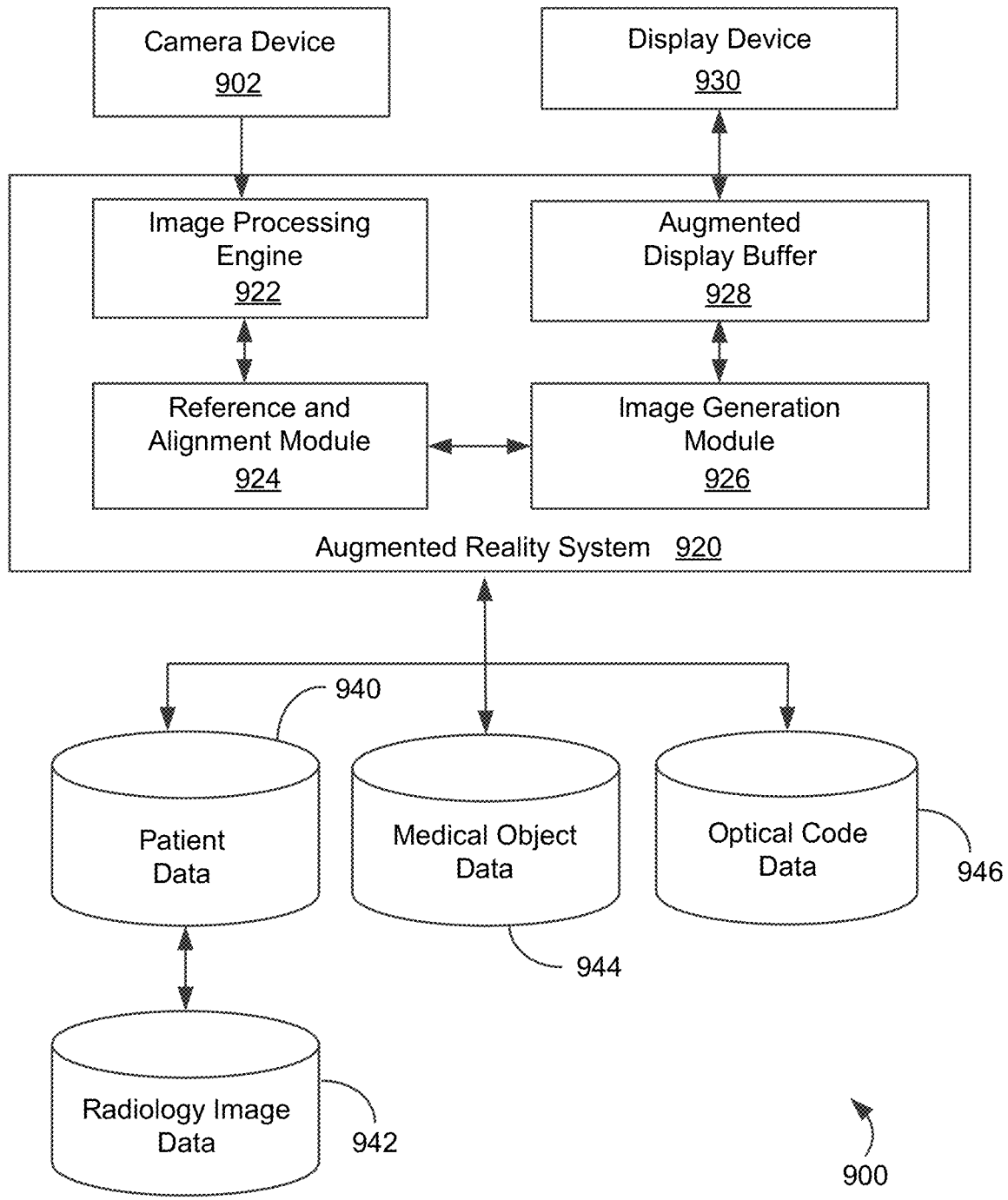
FIG. 9 illustrates an example system that may be employed for aligning an image data set to a body of a person.

FIG. 9 illustrates an example system that may be employed for using an augmented reality (AR) headset to co-localize an image data set with a body of a person which is viewed through the AR headset. The system 900 may include a camera device 902, an augmented reality system 920, a display device 930, and a plurality of databases or data stores. The system 900 may also include one or more processors, a memory, a file system, a communication unit, an operating system, and a user interface, which may be communicatively coupled together. In some embodiments, the system 900 may be, for example, a desktop computer, a server computer, a laptop computer, a smartphone, a tablet computer, an embedded computer, an AR headset, a VR headset, a computing cluster, etc.

The camera device 902 can be configured to capture visible data. In one example, the camera device 902 may be used to capture visible data during a medical procedure or medical examination. The visible data captured by the camera device 902 may include images of a body of a person (or a portion of a body), optical codes, medical implements (e.g., medical instruments, implants, and so on). The camera device 902 may transmit the captured optical data to the augmented reality system 920. The system also may include surface sensors, optical sensors, infrared sensors, Lidar sensors or other sensors to detect and assist with mapping a real view or actual view detected by the AR system. Any object or surface may be detected for an operating theater, a patient, a room, physical geometry, medical implements, or any other physical surroundings or objects.

The augmented reality system 920 may include an image processing engine 922, a reference and alignment module 924, an image generation module 926, and an augmented display buffer 928. For example, the image processing engine 922 may receive the captured visible image data from the camera device 902 and analyzes the visible image data to identify one or more optical codes, objects or people in the visible image data. A plurality of different techniques may be used to identify objects or people within the visible image data including but not limited to feature extraction, segmentation, edge detection and/or object detection.

The image processing engine 922 may identify optical codes that may be affixed to both physical pointer objects and/or bodies of patients within the image. Once the image processing engine 922 identifies an optical code (e.g., an AprilTag, a 2D bar code, a QR code, and so on) the image processing unit 922 accesses the optical code database 946 to retrieve information associated with the optical code. In addition, the optical code may be associated with a particular patient, a particular procedure or a particular object.

In some embodiments, the reference and alignment module 924 may engage with the image processing engine 922 to reference and align a spatial location identified by a physical pointing device and an image data set with respect to each other, as described earlier. In addition, the reference and alignment module 924 can use optical code information in the medical object database 944 to properly identify the size and shape and identity of optical codes. Once the position and orientation of the physical pointing object is determined, the reference and alignment controller 926 can align any associated radiology images in the radiology image data 942 with a spatial location identified by the physical pointing object. In some examples, the radiology images are received from a radiology image database 942 based on patient records in a patient record database 940.

The image generation module 926 can generate graphical data, a virtual laser pointer associated with a physical pointing object, virtual tools, a 3D surgical path, 3D colorization or shading of a mass or organ, or highlighting of a mass, organ or target to display in a display device 930, as layered on top of the body of the patient. In some examples, this information can be loaded into an augmented display buffer 928. This information can then be transmitted to a display device 930 (e.g., an AR headset) for display to a user.

In one example, the patient database 940 includes a plurality of patient records. Each patient record can include one or more medical procedures to be performed on a patient. The patient records may also include notes, instructions or plans for a medical procedure. A patient record can also be associated with one or more radiology images in the radiology image database 942. In some examples, the radiological images include a representation of the virtual anatomical marker that allows the reference and alignment module 926 to properly align the image data set with the body of a patient using the spatial location identified by the physical pointing device. In one example, the medical object data 944 includes information describing the medical implements, including medical instruments, implants, and other objects.

In some embodiments, the augmented reality system may be located on a server and may be any computer system or cluster of computers capable of functioning in connection with an AR headset or display device 930. In such embodiments, the server may be configured to communicate via a computer network with the AR headset in order to convey image data to, or receive data from, the AR headset.

Figure 10:
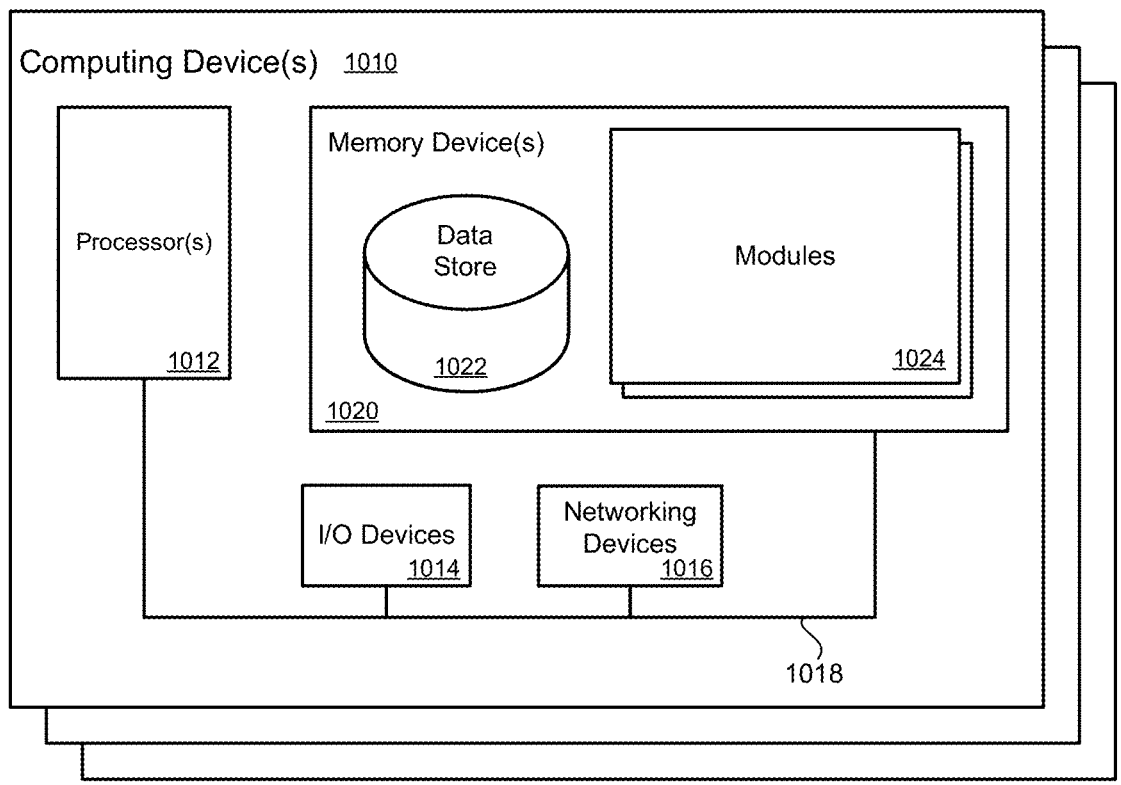
FIG. 10 is a block diagram illustrating an example of a computing system to process the present technology.

FIG. 10 illustrates a computing device 1010 on which modules of this technology may execute. A computing device 1010 is illustrated on which a high-level example of the technology may be executed. The computing device 1010 may include one or more processors 1012 that are in communication with memory devices 1012. The computing device may include a local communication interface 1018 for the components in the computing device. For example, the local communication interface may be a local data bus and/or any related address or control busses as may be desired.

The memory device 1012 may contain modules 1024 that are executable by the processor(s) 1012 and data for the modules 1024. The modules 1024 may execute the functions described earlier. A data store 1022 may also be located in the memory device 1012 for storing data related to the modules 1024 and other applications along with an operating system that is executable by the processor(s) 1012.

Other applications may also be stored in the memory device 1012 and may be executable by the processor(s) 1012. Components or modules discussed in this description that may be implemented in the form of software using high programming level languages that are compiled, interpreted or executed using a hybrid of the methods.

The computing device may also have access to I/O (input/output) devices 1014 that are usable by the computing devices. An example of an I/O device is a display screen that is available to display output from the computing devices. Other known I/O device may be used with the computing device as desired. Networking devices 1016 and similar communication devices may be included in the computing device. The networking devices 1016 may be wired or wireless networking devices that connect to the internet, a LAN, WAN, or other computing network.

The components or modules that are shown as being stored in the memory device 1012 may be executed by the processor 1012. The term "executable" may mean a program file that is in a form that may be executed by a processor 1012. For example, a program in a higher level language may be compiled into machine code in a format that may be loaded into a random access portion of the memory device 1012 and executed by the processor 1012, or source code may be loaded by another executable program and interpreted to generate instructions in a random access portion of the memory to be executed by a processor. The executable program may be stored in any portion or component of the memory device 1012. For example, the memory device 1012 may be random access memory (RAM), read only memory (ROM), flash memory, a solid-state drive, memory card, a hard drive, optical disk, floppy disk, magnetic tape, or any other memory components.

The processor 1012 may represent multiple processors and the memory 1012 may represent multiple memory units that operate in parallel to the processing circuits. This may provide parallel processing channels for the processes and data in the system. The local interface 1018 may be used as a network to facilitate communication between any of the multiple processors and multiple memories. The local interface 1018 may use additional systems designed for coordinating communication such as load balancing, bulk data transfer, and similar systems.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here can also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which can be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

What is claimed is:

1. A method for using an augmented reality (AR) headset to co-localize an image data set with a body of a person, comprising:
    obtaining the image data set of a portion of the body of the person, wherein the image data set includes a virtual anatomical marker to identify an anatomical location and the image data set was captured by a medical imaging device;
    identifying a spatial location using a physical pointer object in a field of view of an optical sensor of the AR headset;
    registering a spatial location of a visible anatomical feature as identified using the physical pointer object, based in part on an input that the physical pointer object is located at a visible anatomical feature of the body of the person; and
    aligning the image data set with the body of the person using the spatial location recorded for the visible anatomical feature as referenced to the virtual anatomical marker in the image data set.

2. The method as in claim 1, further comprising defining a position for the virtual anatomical marker in the image data set using a computing device controlled by a medical professional.

3. The method as in claim 1, wherein the spatial location is at least one of: a point, a curve, a traced area, or a traced three-dimensional (3D) shape.

4. The method as in claim 1, wherein a pointer or tip on the physical pointer object is used to identify the spatial location.

5. The method as in claim 1, wherein a virtual pointer is extended from and controlled by the physical pointer object and a tip of the virtual pointer defines the spatial location.

6. The method as in claim 1, further comprising displaying the image data set visually overlaid on the body of the person using the AR headset.

7. The method as in claim 1, wherein identifying a spatial position of the physical pointer object further comprises identifying a three dimensional (3D) spatial position using the optical sensor of the AR headset.

8. The method as in claim 1, wherein the physical pointer object has an optical code on the physical pointer object to enable the AR headset to determine the spatial position of the physical pointer object.

9. The method as in claim 1, wherein the physical pointer object is a physical wand, a needle, a trocar or a physical object with a pointing tip.

10. The method as in claim 9, wherein a spatial position of the wand can be recognized by the AR headset using an optical code on the wand.

11. The method as in claim 9, wherein a virtual pointer is extended from a finger and a distal end of the virtual pointer is controlled by the finger and the distal end of the virtual pointer represents the tip of the physical pointer object.

12. The method as in claim 1, wherein a spatial location of a tip of the physical pointer object is recognized by detecting edges of the physical pointer object.

13. The method as in claim 1, wherein the physical pointer object is a finger of a medical professional identified by the AR headset.

14. The method as in claim 1, further comprising identifying a spatial location of a tip of a physical pointer object using a fluoroscopic imaging device, wherein the tip of the physical pointer object is touching the visible anatomical feature.

15. The method as in claim 1, further comprising:
    identifying a location of a non-visible anatomical feature within a body of a person using at least two fluoroscopic images;
    inserting a tip of the physical pointer object into the body of the person to touch the anatomical feature;
    registering a location of the tip of the physical pointer object as the spatial location; and
    aligning the image data set with the body of the person using the spatial location recorded for the non-visible anatomical feature as referenced to the virtual anatomical marker in the image data set.

16. The method as in claim 1, wherein the virtual anatomical marker in the image data set is at least one of: a circle, a line, a curve, a spline, a point, crosshairs, a plane, a call-out, a two-dimensional graphic object or a three-dimensional graphic object.

17. The method as in claim 1, further comprising retrieving the image data set automatically for the body of the person using one or more optical codes on the body of the person.

18. The method as in claim 1, wherein an optical code of the physical pointer object includes data or values embedded into the optical code.

19. The method as in claim 1, wherein an optical code of the physical pointer object includes embedded data defining at least one of a medical instrument type, a medical instrument model, a medical instrument version, or a medical instrument manufacturer.

20. The method as in claim 1, wherein an optical code of the physical pointer object includes a unique code for each physical pointer object.

21. The method as in claim 1, wherein values in an optical code of the physical pointer object are used to confirm licensing for at least one of: virtual medical procedure software, alignment software or navigation software.

22. The method as in claim 1, wherein values in an optical code of the physical pointer object are used with optical codes of additional medical instruments to confirm licensing or payments for at least one of: virtual medical procedure software, alignment software or navigation software.

23. The method of claim 1, wherein identifying a spatial location using a physical pointer object, further comprises:
    generating a first virtual plane for the physical pointer object in a first spatial orientation;
    generating a second virtual plane for the physical pointer object in a second spatial orientation;
    generating a third virtual plane for the physical pointer object in a third spatial orientation; and
    calculating an intersection of the first virtual plane, second virtual plane and the third virtual plane, wherein the intersection of the first virtual plane, second virtual plane and the third virtual plane defines the spatial location.

24. The method of claim 1, wherein identifying a spatial location using a physical pointer object, further comprises:

generating a first virtual line for the physical pointer object in a first spatial orientation;

generating a second virtual line for the physical pointer object in a second spatial orientation; and calculating an intersection of the first virtual line and the second virtual line, wherein the intersection of the first virtual line and the second virtual line defines the spatial location.

25. The method of claim 1, further comprising an IR reflector on the physical pointer object, wherein the AR headset projects IR light that reflects from the IR reflector to determine the location of the physical pointer object.

26. The method of claim 1, further comprising an IR light source on the physical pointer object and an IR sensor on the AR headset that is used to determine the location of the physical pointer object.

27. A system for using an augmented reality (AR) headset to co-localize an image data set with a body of a person, comprising:

at least one processor;

at least one memory device including a data store to store a plurality of data and instructions that, when executed, cause the system to:

obtain the image data set of a portion of the body of the person, wherein the image data set is captured by a medical imaging device;

identify a virtual anatomical marker associated with an anatomical feature in the image data set, wherein the virtual anatomical marker has been defined by a medical professional;

identify a physical pointer wand using an optical sensor of the AR headset;

track a spatial position of the physical pointer wand using the optical sensor of the AR headset;

receive input that a pointer of the physical pointer wand is located at a visual anatomical feature;

record a spatial location of a tip of the physical pointer wand at the visual anatomical feature; and align the image data set with the body of the person using the spatial location recorded for the tip of the physical pointer wand as referenced to the virtual anatomical marker in the image data set.

28. The system as in claim 27, wherein a virtual pointer is extended from and controlled by the physical pointer wand and the tip of the virtual pointer defines the spatial location.

29. The system as in claim 27, wherein the physical pointer wand has one or more optical codes on the physical wand to enable recognition of the physical pointer wand.

30. The system of claim 27, wherein the spatial position of the tip of the physical pointer wand is determined by referencing an optical code of the physical pointer wand.

31. The system of claim 27, wherein the tip of the physical wand is recognized by detecting at least a portion of an outline of the physical wand.

32. A non-transitory machine-readable storage medium having instructions embodied thereon, the instructions when executed by one or more processors, cause the one or more processors to perform a process, comprising:

obtaining an image data set of a portion of a body of a person, wherein the image data set is captured by a medical imaging device;

identifying a virtual anatomical marker associated with an anatomical feature in the image data set, wherein the virtual anatomical marker has been defined by a medical professional;

identifying a finger of a user of an augmented reality (AR) headset using an optical sensor of the AR headset;

tracking a position of the finger using the optical sensor of the AR headset;

receiving input from the AR headset that a tip of the finger is pointing at a visible anatomical feature;

registering a spatial location of the finger at the visible anatomical feature; and aligning the image data set with the body of the person using the spatial location recorded for the finger as referenced to the virtual anatomical marker in the image data set.

33. The non-transitory machine-readable storage medium of claim 32, wherein a virtual pointer is a graphical pointer extended from the finger of the user and viewable through the AR headset.

34. The non-transitory machine-readable storage medium of claim 32, wherein the finger has an optical code on the finger to enable recognition of a position of the finger.

* * * * *